(12) United States Patent
Wiedmer et al.

(10) Patent No.: US 6,534,640 B1
(45) Date of Patent: *Mar. 18, 2003

(54) METHODS AND COMPOSITIONS TO ALTER THE CELL SURFACE EXPRESSION OF PHOSPHATIDYLSERINE AND OTHER CLOT-PROMOTING PLASMA MEMBRANE PHOSPHOLIPIDS

(75) Inventors: Therese Wiedmer, Mequon, WI (US); Peter J. Sims, Mequon, WI (US)

(73) Assignee: Blood Center Research Foundation, Milwaukee, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/375,197

(22) Filed: Aug. 16, 1999

Related U.S. Application Data

(63) Continuation of application No. 08/949,246, filed on Oct. 10, 1997, now Pat. No. 6,204,035, which is a continuation-in-part of application No. 08/790,186, filed on Jan. 29, 1997, now Pat. No. 6,172,210.
(60) Provisional application No. 60/015,385, filed on Apr. 2, 1996.

(51) Int. Cl.$^7$ .......................... C07H 21/04; C12N 9/00; C12N 1/20; C12N 15/00; C12N 9/12

(52) U.S. Cl. .................. 536/23.2; 536/23.5; 435/183; 435/194; 435/69.1; 435/252.3; 435/320.1; 935/10; 935/14; 530/350; 530/380

(58) Field of Search ................................ 435/183, 194, 435/69.1, 252.3, 320.1; 935/10, 14; 536/23.2, 23.5; 530/350, 380

(56) References Cited

U.S. PATENT DOCUMENTS

| 5,258,497 A | 11/1993 | Reutelingsperger et al. | 530/350 |
|---|---|---|---|
| 5,552,290 A | 9/1996 | Michelson et al. | 435/7.21 |
| 5,561,070 A | 10/1996 | Stewart et al. | 436/526 |
| 5,578,565 A | 11/1996 | Chao et al. | 514/8 |
| 5,585,380 A | 12/1996 | Bianco et al. | 514/263 |
| 6,204,035 B1 * | 3/2001 | Wiedmer et al. | 435/183 |

OTHER PUBLICATIONS

Bassé, et al., "Isolation of an Erythrocyte Membrane Protein that Mediates $Ca^{2+}$–dependent Transbilayer Movement of Phospholipid," *The Journal of Biological Chemistry* 271(29):17205–17210, 1996.

Bevers, et al., "Platelet Procoagulant Activity: Physiological Significance an Mechanisms of Exposure," *Blood Reviews* 5:146–154, 1991.

Bevers, et al., "Defective $Ca^{2+}$–Induced Microvesiculation and Deficient Expression of Procoagulant Activity in Erythrocytes From a Patient With a Bleeding Disorder: A Study of the Red Blood Cells of Scott Syndrome," *Blood* 79(2):380–388, 1992.

Bevers, et al., "The Complex of Phosphatidylinositol 4,5–Bisphosphate and Calcium Ions Is Not Responsible for $Ca^{2+}$–Induced Loss of Phospholipid Asymmetry in the Human Erythrocyte: A Study in Scott Syndrome, a Disorder of Calcium–Induced Phospholipid Scrambling," *Blood* 86(5):1983–1991, 1995.

Bruckheimer, et al., "Membrane phospholipid asymmetry: host response to the externalization of phosphatidylserine," *Journal of Leukocyte Biology* 59:784–788, 1996.

Chang, et al., "Contribution of Platelet Microparticle Formation and Granule Secretion to the Transmembrane Migration of Phosphatidylserine," *The Journal of Biological Chemistry* 268(10):7171–7178, 1993.

Comfurius, et al., "Reconstitution of Phospholipid Scramblase Activity from Human Blood Platelets," *Biochemistry* 35(24):7631–7634, 1996.

Dachary–Prigent, et al., "Physiopathological Significance of Catalytic Phospholipids in the Generation of Thrombin," *Seminars in Thrombosis and Hemostasis* 22:157–164, 1996.

Devaux, et al, "Maintenance and consequences of membrane phospholipid asymmetry,," *Chem. Phys. Lipids* vol. 73, pp. 107–120, 1994.

Diaz, et al., "Generation of Phenotypically Aged Phosphatidylserine–Expressing Erythrocyted by Dilauroylphosphatidylcholine–Induced Vesiculationk" *Blood* 87(7):2956–2961, 1996.

Fadok, et al., "Exposure of Phosphatidylserine on the Surface of Apoptotic Lymphocytes Triggers Specific Recognition and Removal of Macrophages," *The Journal of Immunology* 148(7):2207–2216, 1992.

Gaffet, et al., "Loss of phospholipid asymmetry in human platelet plasma membrane after 1–12 days of storage," *Eur. J. Biochem.* 222:1033–1040, 1994.

Hamilton, et al., "Complement Proteins C5b–9 Induce Vesiculation of the Endothelial Plasma Membrane and Expose Catalytic Surface for Assembly of the Prothrombinase Enzyme Complex," *The Journal of Biological Chemistry* 265(7):3809–3814, 1990.

Kasukabe, et al., TRA1, a Novel mRNA Highly Expressed in Leukemogenic Mouse Monocytic Sublines But Not in Nonleukemogenic Sublines, *Blood* 89(8):2975–2985, 1997.

Kennedy, et al., "Protection of Porcine Aortic Endothelial Cells from Complement–Mediated Cell Lysis and Activation by Recombinant Human CD59," *Transplantation* 57(10):1494–1501, 1994.

Kojima, et al., "Production and Characterization of Transformed B–Lymphocytes Expressing the Membrane Defect of Scott Syndrome," *J. Clin. Invest.* 94:2237–2244, 1994.

(List continued on next page.)

Primary Examiner—Tekchand Saidha
(74) Attorney, Agent, or Firm—Quarles & Brady LLP

(57) ABSTRACT

A protein preparation that mediates $Ca^{+2}$ transbilayer movement of phospholipid is disclosed. Additionally, a modified or mutated protein preparation, wherein the protein has a reduced ability to mediate transbilayer movement, is disclosed. In a preferred form of the invention, the protein has been modified such that post-translational modification can no longer occur.

2 Claims, 16 Drawing Sheets

OTHER PUBLICATIONS

Koopman, et al., "Annexin V for Flow Cytometric Detection of Phosphatidylserine Expression on B Cells Undergoing Apoptosis," *Blood* 84(5):1415–1420, 1994.

Martin, et al., "Early Redistribution of Plasma Membrane Phosphatidylserine Is a General Feature of Apoptosis Regardless of the Initiating Stimulus: Inhibition by Overexpression of Bcl–2 and Abl," *J. Exp. Med.* 182:1545–1556, 1995.

McIntyre, et al., "Fluorescence Assay for Phospholipid Membrane Assymmetry," *Biochemistry* 30(51):11819–11827, 1991.

Miletich, et al., "Deficiency of Factor $X_1$–Factor $V_a$ Binding Sites on the Platelets of a Patient With a Bleeding Disorder," *Blood* 54(5):1015–1022, 1979.

Sims, et al., "Complement Proteins C5b–9 Cause Release of Membrane Vesicles from the Platelet Surface That Are Enriched in the Membrane Receptor for Coagulation Factor Va and Express Prothrombinase Activity," *The Journal of Biological Chemistry* 263(34):18205–18212, 1988.

Sims, et al., "Assembly of the Platelet Prothrombinase Complex is Linked to Vesiculation of the Platelet Plasma Membrane," *The Journal of Biological Chemistry* 264(29):17049–17057, 1989.

Sims, et al., "Regulatory Control of Complement on Blood Platelets," *The Journal of Biological Chemistry* 264(32):19228–19235, 1989.

Sims, et al, "Induction of Cellular Procoagulant Activity by the Membrane Attack Complex of Complement," *Seminars in Cell Biology* (6):275–282, 1995.

Smeets, et al., "Calcium–induced transbilayer scrambing of fluorescent phospholipid analogs in platelets and erythrocytes,," *Biochem. Biophys. Acta.* vol. 1195, pp. 281–286, 1994.

Toti, et al., "Scott Syndrome, Characterized by Impaired Transmembrane Migration of Procoagulant Phosphatidylserine and Hemorrhagic Complications, Is an Inherited Disorder,", *Blood* 87(4):1409–1415, 1996.

Verhoven, et al., "Mechanisms of Phosphatidylserine Exposure, A Phagocyte Recognition Signal, or Apoptotic T Lymphocytes," *J. Exp. Med.* 182:1597–1601, 1995.

Wang, et al., "Activation of the Alternative Complement Pathway by Exposure of Phosphatidylethanolamine and Phosphatidylserine on Erythrocytes from Sickle Cell Disease Patients," *J. Clin. Invest.* 92:1326–1335, 1993.

Weiss, "Scott Syndrome: A Disorder of Platelet Coagulant Activity," *Seminars in Hematology* 31(4):312–319, 1994.

Weiss, et al., "Platelet Prothrombinase Activity and Intracellular Calcium Responses in Patients With Storage Pool Deficiency, Glycoprotein IIb–IIIa Deficiency, or Impaired Platelet Coagulant Activity—A Comparison With Scott Syndrome," *Blood* 89(5):1599–1611, 1997.

Wiedmer, et al., "On the Mechanism by Which Complement Proteins C5b–9 Increase Platelet Prothrombinase Activity," *The Journal of Biological Chemistry* 261(31):14587–14592, 1986.

Wiedmer, et al., "Complement Proteins C5b–9 Stimulates Procoagulant Activity Through Platelet Prothrombinase," *Blood* 68(4):875–880, 1986.

Wiedmer, et al., "Role of Calcium and Calpain in Complement–Induced Vesiculation of the Platelet Plasma Membrane and in the Exposure of the Platelet Factor Va Receptor," *American Chemical Society* 29(3):623–632, 1990.

Wiedman, et al., "Participation of Protein Kinase in Complement C5b–9–Induced Shedding of Platelet plasma Membrane Vesicles," *Blood* 78(11):2880–2886, 1991.

Wiedman, et al., "Complement–Induced Vesiculation and Exposure of Membrane Prothrombinase Sites in Platelets of Peroxysmal Nocturnal Hemoglobinuria," *Blood* 82(4):1192–1196, 1993.

Williamson, et al., "Continuous Analysis of the Mechanism of Activated Transbilayer Lipod Movement in Platelets," *Biochemistry* 34(33):10448–10455, 1995.

Wood, et al., "Increased Erythrocyte Phosphatidylserine Exposure in Sickle Cell Disease: Flow–Cytometric Measurement and Clinical Associations," *Blood* 88(5):1873–1880, 1996.

Database, Medline on STN, No. 90158550, Zwall, et al., "Loss of membrane phospholipid asymmetry during activation of blood platelets and sickled cells; mechanisms and physiological significance," *Mol. Cell. Biochem.* vol. 1–2, pp. 23–31, 1989.

Zwall, et al., "Pathophysiologic Implications of Membrane Phospholipid Asymmetry in Blood Cells," *Blood* 89(4):1121–1132, 1997.

* cited by examiner

```
  1  cgcggccgcgtcgaccgaaaccagaggagccgcggtgttggcgcaaggttactcccagac
 61  cctttccggctgacttctgagaaggttgcagctgtgccgacagtctgagaggcg
121  cagaagaggaagccatcgcctgccggctctctgaccttgtctcgctcgggagcgga
181  aacagcggcagagaactgttttaatcatggacaaaactcacagatgaatgct
                                  M  D  K  Q  N  S  Q  M  N  A
241  tctcacccggaaacaaactgccagttgggtatcctcagtatccaccgacagcattc
 11  S  H  P  E  T  N  L  P  V  G  Y  P  P  Q  Y  P  P  T  A  F
301  caaggacctccaggatatagtggctacccctggtcagtcagctaccccccacca
 31  Q  G  P  P  G  Y  S  G  Y  P  P  Q  V  S  Y  P  P  P  P
361  gccggccattcaggtcctggcctggcccagtcccaaatcagccagtgtataat
 51  A  G  H  S  G  P  G  P  A  G  F  P  V  P  N  Q  P  V  Y  N
421  cagccagtataatcagccagttggagctgcagggtaccaggatgccagcgccacag
 71  Q  P  V  Y  N  Q  P  V  G  A  A  G  V  P  W  M  P  A  P  Q
481  cctccattaaactgtccacctggattagtcagatactagtcagatactgatt
 91  P  P  L  N  C  P  P  G  L  E  Y  L  S  Q  I  D  Q  I  L
541  catcagcaaattgaacttctggaagttttaacagtttgaaactaacaaatatgaa
111  H  Q  I  E  L  L  E  V  L  T  G  F  E  T  N  N  K  Y  E
601  attaagaacagctttgacagagggttactttgcaggaagatactgattgctgtacc
131  I  K  N  S  F  G  Q  R  V  Y  F  A  A  E  D  T  D  C  C  T
661  cgaaattgctgtgggccatctagacctttacctgaggatattgataatatgggtcaa
151  R  N  C  C  G  P  S  R  P  F  T* L  R  I  I  D  N  M  G  Q
```

FIG. 1A

```
 721  gaagtcataactctggagagaccactaagatgtagcagctgtgttgtccctgctgcctt
 171   E  V  I  T  L  E  R  P  L  R  C  S  C  C  P  C  C  L
 781  caggagatagaatccaagctcctggtcctcctggttatgttattcagacttgg
 191   Q  E  I  E  I  Q  A  P  P  G  V  P  I  G  Y  V  I  Q  T  W
 841  cacccatgtctaccaagtttacaattcaaaatgagaaagaggatgtactaaaaata
 211   H  P  C  L  P  K  F  T  I  Q  N  E  K  R  E  D  V  L  K  I
 901  agtggtccatgtgtgtgcagctgtgtggagatgttgattttgagattttgagaggca
 231   S  G  P  C  V  V  C  S  C  C  G  D  V  D  F  E  I  K  S  L
 961  gatgaacagtgtgtggttgcaaattccaagcactgactgaatttgagaggca
 251   D  E  Q  C  V  V  G  K  I  S  K  H  W  T  G  I  L  R  E  A
1021  tttacagacgctgataacttggaatccagttccctttagacccttgatgtaaatgaaa
 271   F  T  D  A  D  N  F  G  I  Q  F  P  L  D  L  D  V  K  M  K
1081  gctgtaatgattggtgcctgtttcctcattgacttcatgttttgaaagcactggcagc
 291   A  V  M  I  G  A  C  F  L  I  D  F  M  F  F  E  S  T  G  S
1141  caggaacaaaatcaggagtgtgattagtgaagtctcctcaggaaatctgaa
 311   Q  E  Q  K  S  G  V  W  -
1201  gtctgtatattgagactatctaaactcataccctgtgaattactttctgtatactttgat
1261  gtagctctgtgtatactttgtgtttcaattatagttatctttctgtatactgatt
1321  tataaggttttttgtacatttttaatactcattgtcaatttgagaaaaggaacatatga
1381  gttttgcattattaatgaaactccctttgaaaaactgctttaaaaagtcgacgcg
1441  gccgc
```

FIG. 1B

```
  1 tctaaagactcaggaaacaaaacctaaattgcctcaaagttcaggtgctttctccctg
 61 actttagtctagtggagtagtgcagcacctatgcctttctgagaggagtctggagagctg
121 agtcgctgctgtgctaggattctaggaattcgcctcacttgcctagctgcatggagaaaga
181 aaggcttgcaaatggaggctcctcgctcaggaacatacttgccagctgggtatgccctc
  1                                     M  E  A  P  R  S  G  T  Y  L  P  A  G  Y  A  P  Q
241 agtatcctccagcagcagtccaggagacctccagagcatactggacgccccacattccaga
 18   Y  P  P  A  V  Q  G  P  P  E  H  T  G  R  P  T  F  Q  T
301 ctaactaccaagttccccagtctggttatccaggacctcaggctagctacacagtctcaa
 38   N  Y  Q  V  P  Q  S  G  Y  P  G  P  Q  A  S  Y  T  V  S  T
361 catctggacatgaaggttatgctgctacacggcttcctattcaaaataatcagactatag
 58   S  G  H  E  G  Y  A  A  T  R  L  P  I  Q  N  N  Q  T  I  V
421 tcccttgcaaacactcagtggatgccagcaccaccattctgaactgcccacctgggc
 78   L  A  N  T  Q  W  M  P  A  P  P  I  L  N  C  P  P  G  L
481 tagaatacttaaatcagatagatcagcttctgattcatcagcaagttgaacttctagaag
 98   E  Y  L  N  Q  I  D  Q  L  L  I  H  Q  V  E  L  L  E  V
541 tcttaacaggctttgaaacaaatttgaaatcaagaacagcctcgggcagatgg
118   L  T  G  F  E  T  N  N  K  F  E  I  K  N  S  L  G  Q  M  V
601 tttatgttgcagtggagatactgactgctgtgaagcttgctgtgaagctgtctagac
138   Y  V  A  V  E  D  T  D  C  C  T  R  N  C  C  E  A  S  R  P
661 ctttcaccttaagaatcctggatcatcgtgccaagaagtcatgactctgagcgacctc
158   F  T  L  R  I  L  D  H  L  G  Q  E  V  M  T  L  E  R  P  L
721 tgagatgcagtagctgctgctgtgctccccctgcttgcctgcctgctccaggagatagaaatccaggctcctc
178   R  C  S  S  C  C  F  P  C  C  L  Q  E  I  E  I  Q  A  P  P
781 cggggtgccaataggttatgtgactcagactgcaccatgtctgccaaagtctcactc
198   G  V  P  I  G  Y  V  T  Q  T  W  H  P  C  L  P  K  L  T  L
```

FIG. 1C

```
 841  ttcagaacgacaagagggagaatgttctaaagtagttggtcttccatgtgttgcatgcacct
 218    Q  N  D  K  R  E  N  V  L  K  V  V  G  P  C  V  A  C  T  C
 901  gctgttcagatattgactttgagatcaagtctcttgatgaagtgactagaattggtaaga
 238    C  S  D  I  D  F  E  I  K  S  L  D  E  V  T  R  I  G  K  I
 961  tcaccaagcagtggtctgtgttgtgaaagaggccttcacggattcggataacttgga
 258    T  K  Q  W  S  G  C  V  K  E  A  F  T  D  S  D  N  F  G  I
1021  tccaattcccgctagacctggaggtgaagatgaaagctgtgacgcttggtgctgcttcc
 278    Q  F  P  L  D  L  E  V  K  M  K  A  V  T  L  G  A  C  F  L
1081  tcatagattacatgttttgaaggctgtgattaggaacagaaatccgacctgcagtagg
 298    I  D  Y  M  F  F  E  G  C  E  -
1141  aatcaatgaagaagggacagagatctgaagtctacacaaggagatcatatgattgaga
1201  gacctgggcttttgattcttcttcagaatcaagctgttatacatgaa
1261  gcatagtatgtaacatttggtagttcttttacattattggaatag
1321  acctgataattatcttctacacttctaaaataaacattttatgaaaaataagttaaatc
1381  aaagacgaagagagaagtgtatgtttcatctttgttcaattttaaccttgtagtgctgttta
1441  ataatctggattttatttgttactatacatttaccaagttagtttattcttacagaaatcccta
1501  ttataaattgtacttttaattgtactatcaaacctagttagtttatttcttacagaaatccta
1561  ttattttgaaaattacatattttgaaagctttttaaaagatactattgcctgggaaattc
1621  ta
```

FIG. 1D

```
MUR                                                                                        50
HUM  MEAPRSGTYLPAGYAPQYPPAAVQGPPPEHTGRPTFQTNYQVPQSGYPGPQASY

MUR  MDKQNSQMNASHPETNLPVGYPPQYPPTAFQGPPGYSGYPGPQVSYPPPAGHSGPGPA-
                 10         20         30         40         50

MUR                                                      110
HUM  TVSTSGHEGYAATRLPIQNNQTIVLANTQWMPAPPPILNCPPGLEYLNQIDQLLIHQQVE

MUR  GFPVPNQPVYNQ---PV-YNQPVGAAGVPWMPAPQPPLNCPPGLEYLSQIDQILIHQQIE
            60            70         80         90        100       110

MUR                                                                     170
HUM  LLEVLTGFETNNKFEIKNSLGQMVYVAVEDTDCCTRNCCEEASRPFTLRILDHLGQEVMTL

MUR  LLEVLTGFETNNKYEIKNSFGQRVYFAAEDTDCCTRNCCGPSRPFTLRIIDNMGQEVITL
          120        130        140        150        160        170
```

FIG. 5A

```
MUR  ERPLRCSSCCFPCCLQEIEIQAPPGVPIGYVTQTWHPCLPKLTLQNDKRENVLKVVGPCV
     :::::::::::::::::::::::::::::::::::::::::::: :::::: ::::::
HUM  ERPLRCSSCCCPCCLQEIEIQAPPGVPIGYVIQTWHPCLPKFTIQNEKREDVLKISGPCV
          180       190       200       210       220       230
              180       190       200       210       220       230

MUR  ACTCCSDIDFEIKSLDEVTRIGKITKQWSGCVKEAFTDSDNFGIQFPLDLEVKMKAVTLG
     . :::::::::::::::::: .:  ::..:  :::::: :::::::::::.:::::: :
HUM  VCSCCGDVDFEIKSLDEQCVVGKISKHWTGILREAFTDADNFGIQFPLDLDVKMKAVMIG
          240       250       260       270       280       290
              240       250       260       270       280       290

MUR  ACFLIDYMFFEGCE
     :::::: :.:::::
HUM  ACFLIDFMFFESTGSQEQKSGVW
          300
              300       310
```

FIG. 5B

SEQUENCE LISTING

<160> NUMBER OF SEQ ID NOS: 9

<210> SEQ ID NO 1
<211> LENGTH: 1445
<212> TYPE: DNA
<213> ORGANISM: Homo sapiens

<400> SEQUENCE: 1

| | | | | | |
|---|---|---|---|---|---|
| cgcggccgcg | tcgaccgaaa | ccaggagccg | cgggtgttgg | cgcaaaggtt | actcccagac | 60 |
| ccttttccgg | ctgacttctg | agaaggttgc | gcagcagctg | tgcccgacag | tctagaggcg | 120 |
| cagaagagga | agccatcgcc | tggccccggc | tctctggacc | ttgtctcgct | cgggagcgga | 180 |
| aacagcggca | gccagagaac | tgttttaatc | atggacaaac | aaaactcaca | gatgaatgct | 240 |
| tctcacccgg | aaacaaactt | gccagttggg | tatcctcctc | agtatccacc | gacagcattc | 300 |
| caaggacctc | caggatatag | tggctaccct | gggccccagg | tcagctaccc | accccacca | 360 |
| gccggccatt | caggtcctgg | cccagctggc | tttcctgtcc | caaatcagcc | agtgtataat | 420 |
| cagccagtat | ataatcagcc | agttggagct | gcaggggtac | catggatgcc | agcgccacag | 480 |
| cctccattaa | actgtccacc | tggattagaa | tatttaagtc | agatagatca | gatactgatt | 540 |
| catcagcaaa | ttgaacttct | ggaagtttta | acaggttttg | aaactaataa | caaatatgaa | 600 |
| attaagaaca | gctttggaca | gagggtttac | tttgcagcgg | aagatactga | ttgctgtacc | 660 |
| cgaaattgct | gtgggccatc | tagaccttt | accttgagga | ttattgataa | tatgggtcaa | 720 |
| gaagtcataa | ctctggagag | accactaaga | tgtagcagct | gttgttgtcc | ctgctgcctt | 780 |
| caggagatag | aaatccaagc | tcctcctggt | gtaccaatag | gttatgttat | tcagacttgg | 840 |
| cacccatgtc | taccaaagtt | tacaattcaa | aatgagaaaa | gagaggatgt | actaaaaata | 900 |
| agtggtccat | gtgttgtgtg | cagctgttgt | ggagatgttg | attttgagat | taaatctctt | 960 |
| gatgaacagt | gtgtggttgg | caaaatttcc | aagcactgga | ctggaatttt | gagagaggca | 1020 |
| tttacagacg | ctgataactt | tggaatccag | ttccctttag | accttgatgt | taaaatgaaa | 1080 |
| gctgtaatga | ttggtgcctg | tttcctcatt | gacttcatgt | tttttgaaag | cactggcagc | 1140 |
| caggaacaaa | aatcaggagt | gtggtagtgg | attagtgaaa | gtctcctcag | gaaatctgaa | 1200 |
| gtctgtatat | tgattgagac | tatctaaact | catacctgta | tgaattaagc | tgtaaggcct | 1260 |
| gtagctctgg | ttgtatactt | ttgcttttca | aattatagtt | tatcttctgt | ataactgatt | 1320 |
| tataaaggtt | tttgtacatt | ttttaatact | cattgtcaat | ttgagaaaaa | ggacatatga | 1380 |
| gtttttgcat | ttattaatga | aacttccttt | gaaaaactgc | tttaaaaaaa | agtcgacgcg | 1440 |
| gccgc | | | | | 1445 |

<210> SEQ ID NO 2
<211> LENGTH: 318
<212> TYPE: PRT
<213> ORGANISM: Homo sapiens

<400> SEQUENCE: 2

Met Asp Lys Gln Asn Ser Gln Met Asn Ala Ser His Pro Glu Thr Asn
 1               5                  10                  15

Leu Pro Val Gly Tyr Pro Pro Gln Tyr Pro Pro Thr Ala Phe Gln Gly
            20                  25                  30

Pro Pro Gly Tyr Ser Gly Tyr Pro Gly Pro Gln Val Ser Tyr Pro Pro
        35                  40                  45

```
Pro Pro Ala Gly His Ser Gly Pro Gly Pro Ala Gly Phe Pro Val Pro
     50                  55                  60

Asn Gln Pro Val Tyr Asn Gln Pro Val Tyr Asn Gln Pro Val Gly Ala
 65                  70                  75                  80

Ala Gly Val Pro Trp Met Pro Ala Pro Gln Pro Pro Leu Asn Cys Pro
                 85                  90                  95

Pro Gly Leu Glu Tyr Leu Ser Gln Ile Asp Gln Ile Leu Ile His Gln
            100                 105                 110

Gln Ile Glu Leu Leu Glu Val Leu Thr Gly Phe Glu Thr Asn Asn Lys
        115                 120                 125

Tyr Glu Ile Lys Asn Ser Phe Gly Gln Arg Val Tyr Phe Ala Ala Glu
130                 135                 140

Asp Thr Asp Cys Cys Thr Arg Asn Cys Cys Gly Pro Ser Arg Pro Phe
145                 150                 155                 160

Thr Leu Arg Ile Ile Asp Asn Met Gly Gln Glu Val Ile Thr Leu Glu
                165                 170                 175

Arg Pro Leu Arg Cys Ser Ser Cys Cys Pro Cys Cys Leu Gln Glu
            180                 185                 190

Ile Glu Ile Gln Ala Pro Pro Gly Val Pro Ile Gly Tyr Val Ile Gln
        195                 200                 205

Thr Trp His Pro Cys Leu Pro Lys Phe Thr Ile Gln Asn Glu Lys Arg
210                 215                 220

Glu Asp Val Leu Lys Ile Ser Gly Pro Cys Val Val Cys Ser Cys Cys
225                 230                 235                 240

Gly Asp Val Asp Phe Glu Ile Lys Ser Leu Asp Glu Gln Cys Val Val
                245                 250                 255

Gly Lys Ile Ser Lys His Trp Thr Gly Ile Leu Arg Glu Ala Phe Thr
            260                 265                 270

Asp Ala Asp Asn Phe Gly Ile Gln Phe Pro Leu Asp Leu Asp Val Lys
        275                 280                 285

Met Lys Ala Val Met Ile Gly Ala Cys Phe Leu Ile Asp Phe Met Phe
290                 295                 300

Phe Glu Ser Thr Gly Ser Gln Glu Gln Lys Ser Gly Val Trp
305                 310                 315

<210> SEQ ID NO 3
<211> LENGTH: 1622
<212> TYPE: DNA
<213> ORGANISM: Mus musculus

<400> SEQUENCE: 3
tctaaagact caggaaacaa aacctaaatt gcctcaaagt tcaggtgctt tttctccctg    60
actttagtct agtggagtag tgcagcacct atgcctttct gagaggagtc tggagagctg   120
agtcgctgct ggtgctagga ttctaggaat tcgcctcact ggagctgca tgagaaaaga   180 aaggcttgca aatggaggct cctcgctcag gaacatactt gccagctggg tatgcccctc   240
agtatcctcc agcagcagtc caaggacctc cagagcatac tggacgcccc acattccaga   300
ctaactacca agttccccag tctggttatc caggacctca ggctagctac acagtctcaa   360
catctggaca tgaaggttat gctgctacac ggcttcctat tcaaaataat cagactatag   420
tccttgcaaa cactcagtgg atgccagcac caccacctat tctgaactgc ccacctgggc   480
tagaatactt aaatcagata gatcagcttc tgattcatca gcaagttgaa cttctagaag   540
tcttaacagg ctttgaaaca aataacaaat ttgaaatcaa gaacagcctc gggcagatgg   600
```

-continued

```
tttatgttgc agtggaagat actgactgct gtactcgaaa ttgctgtgaa gcgtctagac      660
ctttcacctt aagaatcctg gatcatctgg gccaagaagt catgactctg gagcgacctc      720
tgagatgcag tagctgctgc ttccctgct gcctccagga gatagaaatc caggctcctc       780 cggggggtgcc aataggttat gtgactcaga cctggcaccc atgtctgcca aagctcactc     840
ttcagaacga caagagggag aatgttctaa aagtagttgg tccatgtgtt gcatgcacct      900
gctgttcaga tattgacttt gagatcaagt ctcttgatga agtgactaga attggtaaga     960
tcaccaagca gtggtctggt tgtgtgaaag aggccttcac ggattcggat aactttggga    1020
tccaattccc gctagacctg gaggtgaaga tgaaagctgt gacgcttggt gcttgcttcc    1080
tcatagatta catgtttttt gaaggctgtg agtaggaaca gaaatccgac ctgcagtagg    1140
aatcaatgaa agaggacaga gaagatctga agtctacaca aggagatcat atgattgaga    1200
gacctggggc ttttgattt cttcattgaa atttctcaga atcaagctgt tatacatgaa     1260
gcatagtatg taacattttg gttttcaaat ggtagtttat cttttacatt attggaatag    1320
acctggataa ttatctttat acacttctaa aaatatgcac caaattcaag ttaaaaaaaa    1380
aaagacgaag agaagtgtat gttttaaaat aaaacatttt atggaaaagt aagttaaatc    1440
ataatctggg atttatttt catcttttgt tcaatttaaa ccttgttagt gctgatttta    1500
ttataaaatt gtactttact atcaaaccta gttagtttat ttcttacaga aatcctccta    1560 ttatttgaa attacatatt tttgaaagct ttttaaaaga tactattgcc tgggaaattc     1620
ta                                                                    1622
```

<210> SEQ ID NO 4
<211> LENGTH: 307
<212> TYPE: PRT
<213> ORGANISM: Mus musculus

<400> SEQUENCE: 4

```
Met Glu Ala Pro Arg Ser Gly Thr Tyr Leu Pro Ala Gly Tyr Ala Pro
  1               5                  10                  15

Gln Tyr Pro Pro Ala Ala Val Gln Gly Pro Glu His Thr Gly Arg
                 20                  25                  30

Pro Thr Phe Gln Thr Asn Tyr Gln Val Pro Gln Ser Gly Tyr Pro Gly
         35                  40                  45

Pro Gln Ala Ser Tyr Thr Val Ser Thr Ser Gly His Glu Gly Tyr Ala
     50                  55                  60

Ala Thr Arg Leu Pro Ile Gln Asn Asn Gln Thr Ile Val Leu Ala Asn
 65                  70                  75                  80

Thr Gln Trp Met Pro Ala Pro Pro Ile Leu Asn Cys Pro Gly
                 85                  90                  95

Leu Glu Tyr Leu Asn Gln Ile Asp Gln Leu Leu Ile His Gln Val
                100                 105                 110

Glu Leu Leu Glu Val Leu Thr Gly Phe Glu Thr Asn Asn Lys Phe Glu
        115                 120                 125

Ile Lys Asn Ser Leu Gly Gln Met Val Tyr Val Ala Val Glu Asp Thr
    130                 135                 140

Asp Cys Cys Thr Arg Asn Cys Cys Glu Ala Ser Arg Pro Phe Thr Leu
145                 150                 155                 160

Arg Ile Leu Asp His Leu Gly Asn Glu Val Met Thr Leu Glu Arg Pro
                165                 170                 175

Leu Arg Cys Ser Ser Cys Cys Phe Pro Cys Cys Leu Gln Glu Ile Glu
            180                 185                 190
```

-continued

```
Ile Gln Ala Pro Pro Gly Val Pro Ile Gly Tyr Val Thr Gln Thr Trp
        195                 200                 205

His Pro Cys Leu Pro Lys Leu Thr Leu Gln Asn Asp Leu Arg Glu Asn
        210                 215                 220

Val Leu Lys Val Val Gly Pro Cys Val Ala Cys Thr Cys Ser Asp
225                 230                 235                 240

Ile Ser Phe Glu Ile Lys Ser Leu Asp Glu Val Thr Arg Ile Gly Leu
                245                 250                 255

Ile Thr Leu Gln Trp Ser Gly Cys Val Leu Glu Ala Phe Thr Asp Ser
            260                 265                 270

Asp Asn Phe Gly Ile Gln Phe Pro Leu Asp Leu Glu Val Lys Met Lys
        275                 280                 285

Ala Val Thr Leu Gly Ala Cys Phe Leu Ile Asp Tyr Met Phe Phe Glu
        290                 295                 300

Gly Cys Glu
305

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Peptide
      used to affinity purify 306-318 antibodies

<400> SEQUENCE: 5

Cys Glu Ser Thr Gly Ser Gln Glu Gln Lys Ser Gly Val Trp
  1               5                  10

<210> SEQ ID NO 6
<211> LENGTH: 39
<212> TYPE: DNA
<213> ORGANISM: Artificial Sequence
<220> FEATURE:
<223> OTHER INFORMATION: Description of Artificial Sequence: PL
      scramblase primer

<400> SEQUENCE: 6
tcagaattcg gatccatgga caaacaaaac tcacagatg                          39

<210> SEQ ID NO 7
<211> LENGTH: 43
<212> TYPE: DNA
<213> ORGANISM: Artificial Sequence
<220> FEATURE:
<223> OTHER INFORMATION: Description of Artificial Sequence: PL
      scramblase primer

<400> SEQUENCE: 7
gcttgcctgc aggtcgacct accacactcc tgatttttgt tcc                     43

<210> SEQ ID NO 8
<211> LENGTH: 38
<212> TYPE: DNA
<213> ORGANISM: Artificial Sequence
<220> FEATURE:
<223> OTHER INFORMATION: Description of Artificial Sequence: PL
      scramblase primer

<400> SEQUENCE: 8
tcagaattcg gatccatgga ggctcctcgc tcaggaac                           38
```

```
<210> SEQ ID NO 9
<211> LENGTH: 43
<212> TYPE: DNA
<213> ORGANISM: Artificial Sequence
<220> FEATURE:
<223> OTHER INFORMATION: Description of Artificial Sequence:  PL
      scramblase primer

<400> SEQUENCE: 9
gcttgcctgc aggtcgacct acacacagcc ttcaaaaaac atg                         43
```

METHODS AND COMPOSITIONS TO ALTER THE CELL SURFACE EXPRESSION OF PHOSPHATIDYLSERINE AND OTHER CLOT-PROMOTING PLASMA MEMBRANE PHOSPHOLIPIDS

CROSS-REFERENCE TO RELATED APPLICATION

This application is a continuation of U.S. Ser. No. 08/949,246, filed Oct. 10, 1997, issued as U.S. Pat. No. 6,204,035, which is a continuation-in-part of U.S. Ser. No. 08/790,186, filed Jan. 29, 1997, now U.S. Pat. No. 6,472,210 which claims benefit of U.S. provisional application Ser. No. 60/015,385 filed Apr. 2, 1996. Both of these applications are incorporated by reference as if fully set forth herein.

STATEMENT REGARDING FEDERALLY SPONSORED RESEARCH OR DEVELOPMENT

United States Government may have commercial rights under Grant R01 HL36946 from Heart, Lung, & Blood Institute, National Institutes of Health.

BACKGROUND OF THE INVENTION

The exposure of phosphatidylserine (PS) and other aminophospholipids (aminoPL) on the surface of activated or injured blood cells and endothelium is thought to play a key role in the initiation and regulation of blood coagulation. De novo surface exposure of aminophospholipids has also been implicated in the activation of both complement and coagulation systems after tissue injury, and in removal of injured or apoptotic cells by the reticuloendothelial system. Although migration of these phospholipids (PL) from inner-to-outer plasma membrane leaflets is known to be triggered by elevated intracellular $[Ca^{2+}]$ ($[Ca^{2+}]$) and to be associated with vesicular blebbing of the cell surface, little is known about the cellular constituents that participate in this process.

As described in Ser. No. 08/790,186, cell surface PS has a role in coagulation, programmed cell death and clearance by the reticuloendothelial system. Ser. No. 08/790,186 also describes regulation of the transmembrane distribution of PS, the role of calcium in the collapse of phospholipid asymmetry, and the role PL translocation in Scott Syndrome.

Bassé, et al. and Stout, et al. recently reported the purification and preliminary characterization of an integral RBC membrane protein that, when reconstituted in liposomes, mediates a $Ca^{2+}$-dependent transbilayer movement of PL mimicking plasma membrane PL reorganization evoked upon elevation of $[Ca^{2+}]_c$ (F. Bassé, et al., *J. Biol. Chem.* 271:17205–17210, 1996; J. G. Stout, et al., *J. Clin. Invest.* 99:2232–2238, 1997). Evidence that a protein of similar function must also be present in platelets was recently reported by Comfurius, et al. (P. Comfurius, et al., *Biochemistry* 35:7631–7634, 1996).

Needed in the art is a method for modulating the activity of phospholipid scramblase within a cell, organ or tissue in which one wishes either to reduce the potential for thrombosis, clot formation, or cell clearance (by decreasing cellular PL scramblase expression or activity) or to promote hemostasis or cell clearance (by increasing cellular PL scramblase expression or activity).

BRIEF SUMMARY OF THE INVENTION

The present invention relates to the creation and use of antithrombotic and thrombostatic reagents that rely on the properties of a protein preparation that mediates $Ca^{2+}$-dependent transbilayer movement of membrane phospholipids.

In one embodiment, the present invention is a preparation of a plasma membrane phospholipid scramblase ("PL scramblase"). Preferably, the protein is approximately 35–37 kD as measured on a 12.5% SDS-polyacrylamide gel under reducing conditions. In a most preferred form of this invention, the preparation is a human or a mouse PL scramblase.

In one preferred embodiment of the present invention, the PL scramblase comprises SEQ ID NO:2, representing human PL scramblase, possibly with conservative or functionally equivalent substitutions.

In the most preferred embodiment of the present invention, the PL scramblase, preferably comprising SEQ ID NO:2, has been modified by the action of mammalian cellular enzymes to covalently incorporate phosphorous at one or more Thr, Ser, or Tyr residues or a fatty acid, preferably palmitate, at a cysteine residue.

The present invention is also a preparation of a murine cell protein, wherein the protein is a plasma membrane phospholipid scramblase, preferably wherein the protein is approximately 35 kD as measured on a 12.5% SDS-polyacrylamide gel under reducing conditions.

In one preferred embodiment of the present invention, the murine PL scramblase comprises SEQ ID NO:4, possibly with conservative or functionally equivalent substitutions.

In the most preferred embodiment of the present invention, the murine PL scramblase comprising SEQ ID NO:4 has been modified by the action of mammalian cellular enzymes to covalently incorporate phosphorous one or more Thr, Ser, or Tyr residues, and a fatty acid, preferably palmitate, at a cysteine residue.

The present invention is also a DNA sequence encoding the PL scramblase. Preferably, this DNA sequence comprises SEQ ID NO:1. Most preferably, this DNA sequence comprises residues 211–1164 of SEQ ID NO:1.

The present invention is also a DNA sequence encoding the murine PL scramblase. Preferably, this DNA sequence comprises SEQ ID NO:3. Most preferably, the DNA sequence comprises residues 192–1112 of SEQ ID NO:3.

In another embodiment, the present invention is a method of preventing the surface exposure of plasma membrane phospholipids and reducing the procoagulant properties of a cell by delivering to the cell a mutant phospholipid scramblase. This scramblase is preferably mutated at a site of post-translational modification, most preferably the site is selected from the group consisting of Asp273–Asp284, Thr161 and Cys297 of human PL scramblase SEQ ID NO:2 or the corresponding conserved residues in mouse or other mammalian PL scramblase.

In one embodiment, a gene construct encoding a mutant phospholipid scramblase is delivered to the cell. In an alternative embodiment, the mutant protein itself is delivered.

The present invention is also an inhibitor of the PL scramblase activity of PL scramblase. This inhibitor may be an antisense nucleotide derived from the DNA sequence of PL scramblase. In another embodiment, the inhibitor is a peptide sequence that is a competitive inhibitor of PL scramblase activity. In another embodiment, the inhibitor is an antibody, preferably a monoclonal antibody, raised against PL scramblase.

In another embodiment, the inhibitor works by modifying or inhibiting the post-translational modifications of the PL scramblase that are disclosed below in the Examples. For example, analysis of the primary PL scramblase sequence reveals a potential site of phosphorylation by protein kinase C or other cellular kinase (Thr161), a potential site for acylation by fatty acid (Cys297), and a potential binding site for $Ca^{2+}$ ion provided by an EF-hand-like loop spanning residues Asp273–Asp284. These residues and motifs are conserved 25 in the mouse PL scramblase.

In one embodiment, the inhibitor is a compound that prevents thioacylation of the protein.

In another embodiment, a mutant phospholipid scramblase is provided in which cysteine residues, preferably Cys297 of SEQ ID NO:2 (or the equivalent residue in the conserved region of another PL scramblase), have been replaced by alanine or other non-conservative substitution.

The present invention is also a method for preventing the surface exposure of plasma membrane phosphatidylserine, phosphatidylethanolamine and cardiolipin on the surface of in vitro stored leukocytes, lymphocytes, platelets or red blood cells. This method comprises the steps of adding an inhibitor of PL scramblase activity to the stored blood cells.

The present invention is also a method for prolonging survival of transplanted organs comprising the step of adding an inhibitor of PL scramblase activity to an organ perfusate during in vitro organ storage. The present invention is also a method for prolonging the survival of transplanted cells, tissues, and organs by genetically engineering the cells to be transplanted so as to alter their expression of plasma membrane PL scramblase in order to reduce exposure of PS and other thrombogenic phospholipids at the plasma membrane surface, thereby reducing the risk of infarction due to fibrin clot formation.

The present invention is also a method for prolonging the in vivo survival of circulating blood cells (erythrocyte, platelets, lymphocyte, PMN's, and monocytes) comprising the step of preventing surface exposure of plasma membrane phosphatidylserine on the surface of the cells by exposing the blood cells to an inhibitor of PL scramblase activity.

The present invention is also a method for preventing the procoagulant activities of erythrocytes in sickle cell disease comprising the step of inhibiting erythrocyte PL scramblase in a sickle cell patient.

The present invention is also a method for treating autoimmune and inflammatory diseases comprising the step of treating a patient with an inhibitor of the PL scramblase activity of PL scramblase.

The present invention is also a method for diagnosing individuals with reduced or elevated capacity for platelet-promoted or erythrocyte-promoted fibrin clot activity comprising the step of quantifying the cellular expression of PL scramblase. This quantitation may take the form of immunoblotting using an antibody to PL scramblase, an ELISA assay using an antibody to PL scramblase, flow cytometric analysis of the binding of monoclonal antibody reactive against the predicted extracellular domain of PL scramblase (residues Ser310–Tryp318 of sequence disclosed in SEQ ID NO:2 or the equivalent residue in the conserved region of another PL scramblase) or using oligonucleotides derived from PL scramblase cDNA and the polymerase chain reaction. In one method of the present invention, the quantitation is performed by isolating PL scramblase from a patient blood sample, measuring the amount of PL scramblase isolated and comparing the measurement with a control sample. The measurement may be by isolating PL scramblase from a patient blood sample and measuring via densitometry the amount of PL scramblase protein electrophoresed in a stained electrophoretic gel.

It is an object of the present invention to provide a preparation of a PL scramblase.

It is another object of the present invention to genetically alter the level of expression of PL scramblase by delivery of cDNA representing sense or antisense nucleotide sequence ligated into a suitable mammalian expression vector.

It is another object of the present invention to provide an inhibitor of PL scramblase PL scramblase activity.

It is another object of the present invention to provide an antithrombotic agent.

It is another object of the present invention to create cells, tissue, and organs for transplantation that have increased potential for survival and reduced potential for causing fibrin clot formation and vascular thrombosis when grafted into a recipient host.

It is another object of the present invention to create an animal, preferably a mouse or pig, that has been genetically engineered so that the PL scramblase gene is not expressed.

Other objects, advantages and features of the present invention will become apparent after one of skill in the art reviews the specification, claims and drawings herein.

BRIEF DESCRIPTION OF THE SEVERAL VIEWS OF THE DRAWINGS

FIGS. 1A and 1B are comparisons of the cDNA and deduced amino acid sequence of human PL scramblase (SEQ ID NOs:1 and 2).

FIGS. 1C and 1D are comparisons of the cDNA and deduced amino acid sequence of murine PL scramblase (SEQ ID NOs:3 and 4).

FIGS. 5A and 5B are comparisons of protein sequences of mouse and human PL scramblase (SEQ ID NOs:2 and 4).

FIG. 9A depicts fluorescence of cells expressing GFP.

DETAILED DESCRIPTION OF THE INVENTION

Figure 2:
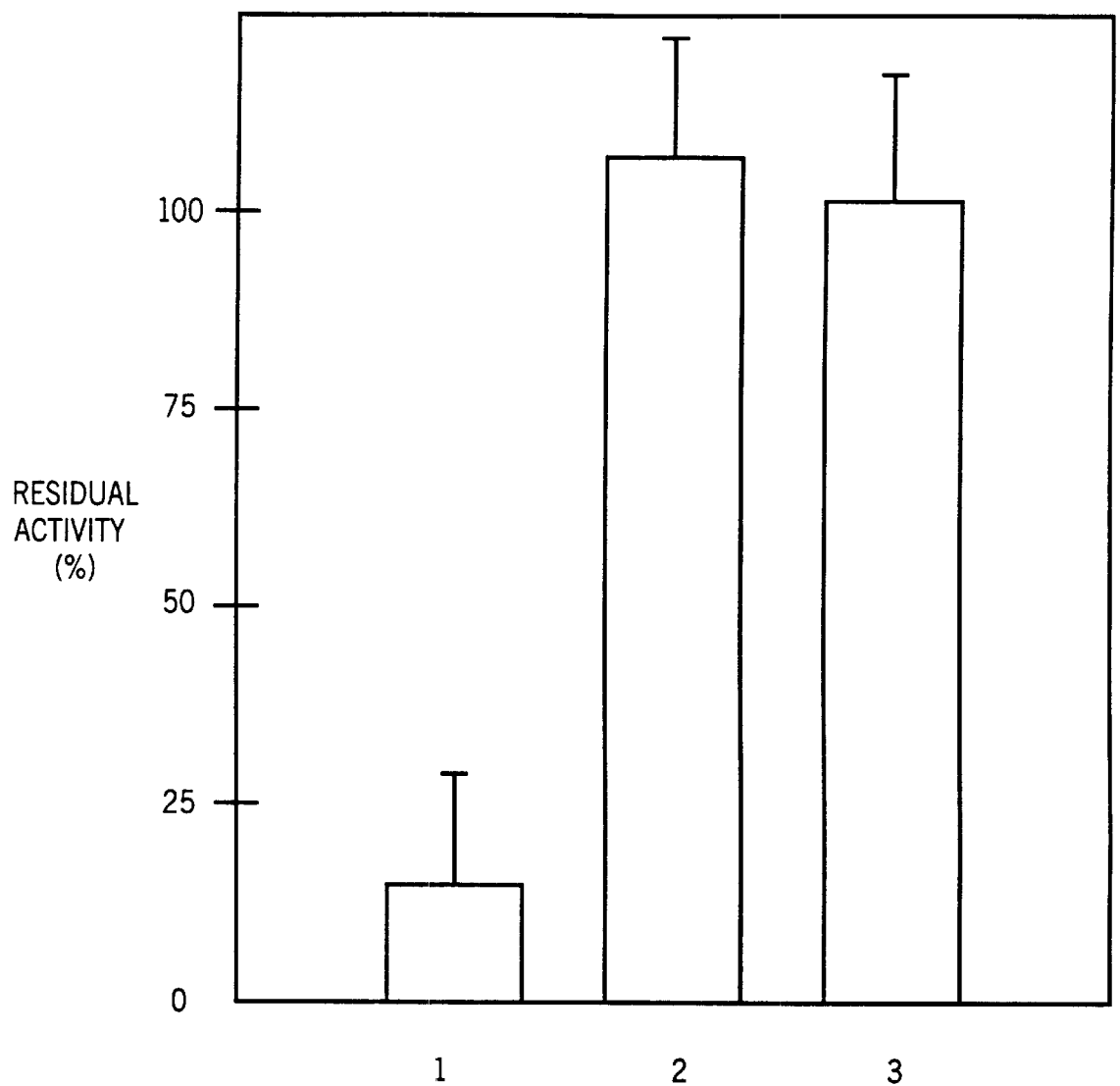
FIG. 2 is a bar graph illustrating immunoprecipitation of erythrocyte PL scramblase.

In the description of the invention presented herein, Applicants specifically refer to numerical residue positions in both the PL scramblase amino acid and nucleotide sequence. These reference numbers refer to the residue position in the amino acid or nucleotide sequence listed in the Sequence Listing. When Applicants use these reference numbers to describe a proposed mutated PL scramblase or nucleic acid, Applicants mean for these reference numbers to refer to the comparable or equivalent residue in that protein or amino acid. For example (see FIG. 5), threonine 161 in the human protein sequence (SEQ ID NO:2) is equivalent to threonine 159 in the mouse protein sequence (SEQ ID NO:4). Although these residues have different reference numbers, they are equivalent residues in the two sequences based upon conserved homology in the aligned sequences. One may determine what a "equivalent residue" is in an unknown PL scramblase sequence by deducing the highest probability alignment to the human sequence using BLAST, FASTA or other sequence alignment tool commonly known to those skilled in the art.

1. PROTEIN PREPARATION AND NUCLEIC ACID SEQUENCES

The Examples below disclose the purification and preliminary characterization of an integral RBC membrane protein that, when reconstituted in liposomes, mediates a $Ca^{2+}$-dependent transbilayer movement of PL mimicking plasma membrane PL reorganization evoked upon elevation of $[Ca^{2+}]_c$. Based on internal peptide sequence obtained from the purified erythrocyte PL scramblase protein, we cloned the cDNA (SEQ ID NO:1) encoding this protein from a human K-562 erythroleukemic library (Q. Zhou, et al., *J. Biol. Chem.* 272:18240–18244, 1997). The deduced human PL scramblase protein (SEQ ID NO:2) is a single chain polypeptide of 318 amino acids with molecular weight of 35.1 kD and calculated isoelectric point of 4.9. It is predicted to be a type 2 membrane protein with a single transmembrane domain near the carboxyl terminus (residues Ala291–Gly309), a short exoplasmic carboxyl terminal peptide (residues Ser310–Trp318) with the remaining polypeptide (residues Met1–Lys290) in the cytosol.

The present invention involves the purification and characterization of this approximately 35–37 kD membrane protein that promotes a $Ca^{2+}$-dependent transbilayer redistribution of membrane phospholipids including PS and PC, with properties similar to the PL scramblase activity that is evoked upon elevation of $Ca^{2+}$ in the cytosol of erythrocytes and other cells. We have named this membrane protein "P37." We mean for "P37" to be synonymous with "phospholipid scramblase" or "PL scramblase" and refer to these names interchangeably throughout the text. By "phospholipid scramblase" or "PL scramblase activity," we mean the $Ca^{2+}$ dependent transbilayer movement of plasma membrane phospholipid.

In one embodiment, the present invention is a protein preparation of PL scramblase. In preferred embodiments of the present invention, the preparation is of either human or mouse PL scramblase.

If one desires the human PL scramblase, preferably, the protein comprises residues 1–318 of SEQ ID NO:2. More preferably, the PL scramblase comprises residues 85–307 of SEQ ID NO:2, representing only the most highly conserved residues of the human PL scramblase when aligned against murine PL Scramblase (see FIG. 5).

If one desires the mouse PL scramblase, preferably, the protein comprises residues 1–307 of SEQ ID NO:4. More preferably, the PL scramblase comprises residues 83–307 of SEQ ID NO:4, representing only the most highly conserved residues of the mouse PL scramblase when aligned against human PL Scramblase (see FIG. 5).

In another embodiment, the protein comprises conservative substitutions or functionally equivalent residues of the residues described in the paragraph above. By "functionally equivalent" we mean that the equivalent residues do not inhibit or disrupt the activity of the PL scramblase preparation. A protein with "equivalent" substitutions would have at least a 10%, preferably 50%, activity of a native PL scramblase preparation.

The Examples below demonstrate one method of isolating PL scramblase from human erythrocytes. After examination of the specification below, other methods of protein isolation will become apparent to one of skill in the art. The Examples below also describe an assay for the measurement of PL scramblase activity. A suitable preparation of the present invention would have a PL scramblase activity of at least 10% that of the preparation described below in the Examples. Preferably, the activity would be at least 50% that of the Examples described below.

We specifically envision that one may wish to isolate the PL scramblase from a variety of mammalian sources including human, mouse, pig, or other mammal.

In one embodiment of the invention, the PL scramblase is isolated from erythrocyte membranes. In another embodiment, the protein is isolated from one or more body tissues including, spleen, skin, lung or other organ. In another embodiment, the protein is produced by bacteria cells, such as *E. coli* cells, insect cells, or yeast, preferably in vitro cultures that are transfected with plasmid or viral vectors containing cDNA sequences identified at SEQ ID NOs:1 or 3 in the correct reading frame. The vector can be chosen from among protein expression vectors known to those skilled in the art. Preferable viral vectors include retrovirus, adenovirus, and baculovirus vectors.

The present invention is also a recombinant DNA sequence encoding PL scramblase. A preferable DNA sequence encoding PL scramblase would comprise the residues of SEQ ID NO:1 (human sequence) or SEQ ID NO:3 (mouse sequence). A more preferable DNA sequence encoding PL scramblase would comprise the nucleic acids 211–1164 of SEQ ID NO:1 or 192–1112 of SEQ ID NO:3. The most preferred DNA sequence encoding PL scramblase would comprise the nucleic acids 463–1137 of SEQ ID NO:1 or 438–1112 of SEQ ID NO:3

One of skill in the art of molecular biology would know how to obtain other DNA sequences encoding the PL scramblase. For example, one might sequence PL scramblase directly via standard protein sequencing techniques. The peptide sequence could be analyzed to provide oligonucleotide probes for a human cDNA leukocyte library. (One such cDNA library is available from Invitrogen in a pCDNA3 vector.)

By use of probes obtained from these and other the PL scramblases, one would then be able to isolate other cDNA clones encoding the entire PL scramblase protein sequence from a species or cell culture of interest. SEQ ID NO:1 contains the entire open reading frame encoding human PL scramblase as well as flanking residues of 5' and 3' untranslated sequence. The full-length translation of SEQ ID NO:1 is identified as SEQ ID NO:2. In the cDNA, this translated sequence would normally be followed by the appropriate stop codon.

Based on the nucleotide sequence of human PL scramblase, the Examples below disclose a full-length cDNA for murine PL scramblase from a mouse fibroblast cDNA library (CLONETECH). The resulting cDNA (SEQ ID NO:3) predicts an open reading frame encoding a 307 residue polypeptide (molecular weight 33.9 kDa; calculated pI=4.9) (SEQ ID NO:4). Analysis of the murine PL scramblase protein revealed that it had virtually the same apparent affinity for $Ca^{2+}$ and the same activity in promoting transbilayer movement of phospholipids as exhibited by the recombinant human protein.

Alignment of the murine and human PL scramblase proteins reveals 65% overall identity of sequence, with the most divergent sequence found in the amino terminal portion of the protein. The murine carboxyl terminus is truncated, and does not include the predicted exoplasmic domain found in the carboxyl terminus of human PL scramblase. This suggests that residues Ser310–Trp318 in human PL scramblase do not contribute to its function.

By contrast, segments of human PL scramblase polypeptide that are implicated to participate in its phospholipid mobilizing function (detailed below), are highly-conserved in the mouse protein. These structural motifs that are conserved in both human and mouse PL scramblase include: a single inside-outside transmembrane domain for membrane attachment (human residues Ala291–Gly309); a potential site of phosphorylation by protein kinase C or other cellular kinase (Thr161 in human); a potential site of thiol-acylation with palmitic acid (Cys297 in human); and a potential binding site for $Ca^{2+}$ ion (residues Asp273–Asp284 in human). Based on the best fit alignment of the human and mouse protein sequences reported as SEQ ID NO:2 and SEQ ID NO:4, we deduce that the highly-conserved portions of the polypeptide, representing residues 85–309 of SEQ ID NO:2 of human PL scramblase and residues 83–307 of SEQ ID NO:4 (i.e., the equivalent residues of mouse PL scramblase) contains the portion of the protein required for PL scramblase activity.

The present invention is also a preparation of a modified or mutated PL scramblase wherein the PL scramblase has a reduced ability to mediate transbilayer movement of lipids. By "reduced activity" we mean that the modified scramblase has less than 10% of the activity of the wild-type scramblase. Preferably, this activity is measured by the $Ca^{2+}$ dependent movement of fluorescent phospholipids in reconstituted proteoliposomes (see Examples 1 and 2). More preferably, this activity is measured by the intracellular $Ca^{2+}$-dependent movement of PS to the cell surface in cells treated or transfected so as to express a modified or mutated PL scramblase (see Example 3).

Preferably, the protein is modified such that it is o longer post-translationally modified, as described above. Most preferably, the modification occurs at amino acid residue Thr161, Cys297, or Asp273–Asp284.

The present invention is also a recombinant nucleic acid encoding a modified or mutated scramblase.

2. MODULATORS OF PL SCRAMBLASE ACTIVITY

The present invention is also a modulator, either an inhibitor or enhancer, of the PL scramblase activity of PL scramblase. The information below in the Examples demonstrates a new understanding of the post-translational modification of PL scramblase that may be used to design methods of modulating PL scramblase activity and mutated PL scramblases with modified scramblase activity. For example, analysis of the primary PL scramblase sequence reveals a potential site of phosphorylation by protein kinase C or other cellular kinase (Thr161), a potential site for acylation by fatty acid (Cys297), and a potential binding site for $Ca^{2+}$ ion provided by an EF-hand-like loop spanning residues Asp273–Asp284. Knowledge of these post-translational modifications allows one to design specific inhibitors or modulators of the PL scramblase activity.

Therefore, as elaborated below in sections A, B and C, the present invention is a method of modulating PL scramblase activity by disrupting specific post-translational modifications. In one embodiment, the method comprises exposing a PL scramblase molecule to a post-translational modification inhibitor and, thus, reducing PL scramblase activity. This method will be useful in a variety of applications where reduction of the rate of clearance of a cell from the body or a reduction in clot promoting and procoagulant activities of a cell is desired. Among the post translational modification predicted to alter the activity of PL scramblase include insertion of the protein into phospholipid membranes, phosphorylation of the polypeptide by an intracellular protein kinase at one or more Tyr, Thr, or Ser residues, the addition of palmitate or other fatty acid by thioacylation through formation of a thioester bond at one or more Cys residues in the cytoplasmic or transmembrane domains of the protein, the binding of one or more metal ions to the protein, the aggregation of the protein with itself or one or more cofactors, proteolytic degradation of the protein by one or more cytoplasmic proteases including by example calpains or caspases.

In another embodiment, the method comprises creating a gene construct encoding a modified PL scramblase. The scramblase will be modified at the site of the post-translational modification described above. This modified gene may be used to transfect cells that one wishes to display a reduction of clot promoting or procoagulant activities or to prolong the survival of the cell in the body.

Sections A, B and C below describe specific residues that one may wish to mutate. One of skill in the art would be aware of general molecular biological techniques that would enable one to acquire a PL scramblase gene, create the appropriate mutation, create the appropriate genetic construct, and transform the desired cell line.

In another embodiment, the inhibitor is an antisense nucleotide derived from the DNA sequence encoding PL scramblase. One of skill in the art would know how to create such an antisense nucleotide from the cDNA sequence of PL scramblase.

In another embodiment, the inhibitor is an antibody, preferably a monoclonal antibody, raised against PL scramblase. One of skill in the art would know how to make an antibody preparations from the purified protein preparation described below.

A. Cysteine Thioester

Our discovery of the presence of a conserved site for Cys thiol-acylation in the transmembrane domains of human and mouse PL scramblase (Cys297 in human) suggests that PL scramblase polypeptide is post-translationally modified by the attachment of fatty acid, and that this thiol-acylation is required for normal expression of its biological activity. Attachment of fatty acid (predominantly palmitic acid) by acylation of the cysteinyl thiol residue has been shown to regulate the biological activity of a variety of cellular proteins (G. Milligan, et al., *Trends Biochem. Sci.* 20:181–185, 1995; M. J. Schlesinger, et al., In: *Lipid Modification of Proteins*, pp. 1–19, CRC Press, Boca Raton, Fla. 1993).

One embodiment of the present invention is a method to prevent egress of PS and other clot-promoting and procoagulant phospholipids to cell surfaces by preventing or reversing the acylation of cysteines in plasma membrane PL scramblase protein. In one embodiment of the present invention, one would create a mutated scramblase, wherein cysteine 297 (or the equivalent residue in the conserved region of another PL scramblase) is no longer available for post-translational modification. This may be by substituting the cysteine with a alanine, serine or another non-functionally equivalent amino acid residue. The cDNA encoding this mutated scramblase may be placed in a vector expression system and used to transfect cells of interest. We envision that the mutated scramblase will out-compete native scramblase and, thus, reduce scramblase activity.

In another embodiment, the method preferably comprises the steps of exposing a PL scramblase to a thiolacylation inhibitor and inhibiting PL scramblase activity. Applicants note that the thiolacylation inhibitor could either inhibit thiolacylation directly, block the site of thiolacylation, or hydrolyze pre-existing thioester-linked fatty acids attached to the protein. Applicants specifically envision that the thiolacylation may be prevented by compounds selected from the class of specific antibodies against the protein that react at the site of thioacylation, thiol-reactive compounds that covalently modify cysteine residues (including by example N-ethyl maleimide, iodoacetamide, or pyridyldithioethylamine), an inhibitor of enzyme acyltransferases including by example an esterase inhibitor chosen from among carbamates (e.g., physostigmine)and organophosphorus (e.g., diisopropylfluorophosphate) compounds that are reactive at the active site of such enzymes. Such a method will be useful for many of the objects described above, such as treating cells, tissues, and organs for transplantation to reduce potential for causing fiber and clot formation in vascular thrombosis when grafted into a recipient host. The method could also be used to provide an antithrombotic therapeutic effect. The method could also be used to increase in vivo survival of the transfused or transplanted cell by suppressing exposure of PS or other aminophospholipids at the cell surface.

B. Peptide Residues Involved in Binding $Ca^{2+}$

The phospholipid transport function of PL scramblase is activated by $Ca^{2+}$ with apparent affinity of 50–100 micromolar, implying a relatively low affinity binding site for the calcium ion within the polypeptide (Q. Zhou, et al., *J. Biol. Chem.* 272:18240–18244, 1997; J. G. Stout, et al.,*J. Clin. Invest.* 99:2232–2238, 1997; F. Bassé, et al., *J. Biol. Chem.* 271:17205–17210, 1996). The deduced protein sequence of mouse and human PL scramblase reveals an extensive segment of highly conserved sequence extending through residue Glu306 (or the equivalent residue in the conserved region of another PL scramblase). The predicted secondary structure through this portion of the protein reveals that it contains two short alpha-helical segments near the C-terminus that are separated by a 12-residue acidic loop. In both proteins (human and mouse), the C-terminal alpha helix represents a predicted transmembrane segment with a strongly-preferred inside-to-outside orientation, whereas sequence contained within the adjacent 12-residue acidic loop conforms in-part to a consensus sequence that is characteristic of an EF-hand $Ca^{2+}$-binding motif (S. Nakayama, et al., *Annu. Rev. Biophys. Biomol. Struct.* 23:473–507, 1994). In this motif, residues in positions 1, 3, 5, 7, 9 and 12 contribute to octahedral coordination of the $Ca^{2+}$ ion, with the residues in position 1[Asp], 3[Asp, Asn, or Ser] and 12 [Asp or Glu] being those most highly conserved. In order to gain insight into whether this segment of the protein might be directly involved in the $Ca^{2+}$-dependent reorganization of membrane PL mediated by PL scramblase, we expressed mutant human PL scramblase with Asp→Ala substitutions at positions corresponding to residues 1 (i.e., Asp273), 3 (i.e., Asp275), and 12 (i.e., Asp284) of this putative 12 residue EF-hand loop. Whereas mutations in positions 1 or 12 lead to a partial loss of function, mutation in position 3 resulted in complete inactivation of the $Ca^{2+}$-dependent response. The partial loss in activity of PL scramblase with mutations in positions 1, 3, or 12 was accompanied by a significant reduction in apparent avidity for $Ca^{2+}$. These.data identify the segment of human PL scramblase between Asp273–Asp284 as containing the essential binding site for $Ca^{2+}$ and suggest that the activity of this protein can be selectively inhibited by blocking-access of $Ca^{2+}$ to this segment of the polypeptide or by modifying residues contained in this segment of the polypeptide.

Therefore, in another embodiment, the present invention is a method for inhibiting the clot-promoting and procoagulant activity of the plasma membrane by preventing the binding of intracellular $Ca^{2+}$ to the PL scramblase polypeptide. In one embodiment, the method comprises constructing a mutant PL scramblase, wherein the PL scramblase is mutated between Asp273 and Asp284 so that the scramblase does not bind $Ca^{2+}$ with the same affinity as PL scramblase. This mutant gene may be used, by methods known to one of skill in the art, to transfect a cell or cell line in which one wishes to modulate the clot promoting or procoagulant properties. We envision that the mutated PL scramblase will out-compete native PL scramblase and thus modulate, preferably reduce, PL scramblase activity in the cell or cell line.

In another embodiment, this method preferably comprises the steps of exposing a PL scramblase to a calcium binding inhibitor and reducing PL scramblase activity. Applicants specifically envision that this inhibitor may be either a direct inhibitor of calcium binding or would bind to the residues described above and block calcium binding. This method, as above, would be useful to prepare cells, tissues and organs for transplantation and as a therapeutic antithrombotic.

C. Modification of PL Scramblase Through Phosphorylation by Cellular Protein Kinases As another embodiment, the present invention includes a method to prevent phosphorylation of PL scramblase at one or more Tyr, Thr or Ser residues by inhibiting the action of intracellular Tyr or Ser/Thr kinases. The amino acid sequence of PL scramblase reveals potential sites of phosphorylation at Tyr, Thr, or Ser residues by cellular protein kinases, including the conserved motif Thr161–Leu162–Arg163 of human SEQ ID NO:2 (corresponding to Thr159–Leu160–Arg161 of mouse SEQ ID NO:4) predicting phosphorylation by protein kinase C (Q. Zhou, et al., supra, 1997 and FIG. 5). Protein phosphorylation by one or more cellular protein kinases is known to regulate many aspects of cell function, which can include both the activation and inactivation of specific enzyme activities. In the specific case of PL scramblase, depletion of cellular ATP has been shown to inhibit surface exposure of phosphatidylserine on erythrocytes exposed to elevated $[Ca^{2+}]_c$ (D. W. Martin, et al. ,*J. Biol. Chem.* 270:10468–10474, 1995). In combination with our discovery of conserved motifs for phosphorylation of PL scramblase, we propose that normal PL scramblase activity requires constitutive phosphorylation of the polypeptide. Such phosphorylations invariable occur at one or more tyrosines (ie., by tyrosine protein kinases) or at one or more serines or threonines (i.e. by Ser/Thr protein kinases). The specific sites of phosphorylation within a given protein are readily identified by finding conserved sequence motifs predictive of phosphorylation, and confirmed using methods known to those skilled in the art. Such methods include metabolically labeling the cellular proteins with $^{32}p$, purifying the protein using specific antibody, and identifying the specific residues of polypeptide sequence that contain covalently bound $^{32}p$, standardly performed by tryptic cleavage of the isolated protein, HPLC separation of resulting peptides, and identification of the phosphorylated residues by either Edman degradation or mass spectroscopic analysis.

As another embodiment, the Examples below specifically disclose Thr161 (or the equivalent residue in the conserved region of another PL scramblase) as a single predicted site of phosphorylation by protein kinase C. Disruption of this phosphorylation or modification of the particular residues involved would modify PL scramblase activity. Therefore, the present invention is a method for altering the procoagulant activity of the plasma membrane by preventing phosphorylation by protein kinases, such as protein kinase C. In one embodiment, the method comprises creating a mutant PL scramblase, wherein the mutant PL scramblase does not contain a site capable of phosphorylation by cellular protein kinase. Preferably, the mutant PL scramblase is mutated at Thr161. One then creates a gene construct capable of expressing the mutated PL scramblase and transfects a cell or cell line of interest. In this manner, one introduces a mutant PL scramblase into the cell or cell line and out competes native or wild-type PL scramblase, thus altering the PL scramblase activity of the cell. In another embodiment, the method preferably comprises the steps of exposing a PL scramblase to a phosphorylation inhibitor and thus altering PL scramblase activity. Applicants specifically envision that this inhibitor may be either a general phosphorylation inhibitor or may specifically block phosphorylation at Thr161. As described above, the method would be useful to prepare cells tissues and organs for transplantation and as a therapeutic antithrombotic.

3. EXPRESSION OF PC SCRAMBLASE IN HUMAN PLATELET, HUMAN ENDOTHELIUM AND OTHER CELL TYPES

Our results described below in the Examples confirm that the level of expression of plasma membrane PL scramblase can determine the extent to which PS is mobilized to the cell surface upon elevation of $[Ca^{2+}]_c$, and suggest that this protein normally functions to mediate the redistribution of plasma membrane phospholipids in response to the entry of calcium into the cytosol.

These data provide the first experimental demonstration that the cellular potential to mobilize PS and other procoagulant aminophospolipids from plasma membrane inner leaflet to the cell surface—and thereby expose binding sites for factor Va or other plasma coagulation factor—can be manipulated by selectively altering the level of expression of a particular cellular protein, either through direct transfection with the PL scramblase cDNA, by another intervention affecting either total cellular expression of PL scramblase protein or a post-translational modification of the PL scramblase polypeptide that is essential for its PS mobilizing function in the plasma membrane.

In one embodiment, the present invention is a method of either increasing or decreasing the clot-promoting and procoagulant properties of cell surfaces by either increasing or decreasing the level of cellular expression PL scramblase mRNA and protein.

4. OTHER EMBODIMENTS

The present invention is also a method for preventing the surface exposure of plasma membrane phospholipids, such as phosphatidylserine, phosphatidylethanolamine and cardiolipin, on the surface of in vitro stored blood cells (including, platelets, red blood cells, lymphocytes, or leukocytes) by adding an inhibitor or modulator of the PL scramblase activity of PL scramblase to the stored cells.

The present invention is also a method for prolonging survival of transplanted organs and grafts comprising the step of adding an inhibitor of PL scramblase PL scramblase activity to an organ perfusate during in vitro organ storage. The present invention is also a method for prolonging the survival of transplanted cells, tissues, and organs by genetically engineering the cells to be transplanted so as to alter their expression of plasma membrane PL scramblase in order to reduce exposure of PS and other thrombogenic phospholipids at the plasma membrane surface, thereby reducing the risk of infarction due to fibrin clot formation.

Therefore, in one embodiment, the present invention is a genetically engineered cell for transplantation into a human or animal wherein the cell has a lowered PL scramblase expression. Preferably, the cell expresses no PL scramblase. Preferably, this cell comprises a nucleotide molecule which is expressed by the cell and which codes for protein inhibiting the activity of PL scramblase. In another preferable embodiment, the promotor of the PL scramblase gene is altered to either increase or decrease the expression of the gene. One of skill in the art of molecular biology would envision methods to create these altered cells.

The present invention is also an animal, such as a mouse or pig, that has been genetically manipulated to "knock out" PL scramblase expression. Such an animal may be created by many variations of techniques known to one of skill in the art. Most preferably, one would delete by homologous recombination one or more exons of the PL scramblase gene within the chromosomal DNA of the appropriate embryonic stem cell of mouse, pig, or other animal. In the mouse, those exons most favored for deletion by homologous recombination are those that include part or all of DNA sequence between residues 438–1112 of SEQ ID NO:3, representing the conserved portion of the cDNA open reading frame required for expression of functional PL scramblase protein. Those embryonic stem cells showing the PL scramblase gene deletion are surgically implanted within the uterus at the appropriate time in the estrus cycle. The resulting animals carrying the defective gene are then bred to homozygosity for the PL scramblase gene deletion defect.

Preferably, the engineered cell is selected from the group consisting of endothelial cells, fibroblasts, epithelial cells, skeletal cells, cardiac and smooth muscle cells, hepatocytes, pancreatic islet cells, bone marrow cells, astrocytes, and Schwann cells. The present invention is also a prosthesis for implantation in an animal or human having the genetically engineered cells attached thereto. In one embodiment, the prosthesis is a vascular graft.

The present invention is also a method for prolonging the in vivo survival of circulating blood cells comprising the step of preventing surface exposure of plasma membrane phosphatidylserine on the circulating blood cells by inhibiting the function of plasma membrane PL scramblase. One may also wish to prevent the procoagulant properties of erythrocytes in sickle cell disease by inhibiting erythrocyte PL scramblase in a sickle cell patient.

The present invention is also a method for treating autoimmune and inflammatory diseases, such as disseminated intravascular coagulation, vascular thrombosis, fibrin generation during cardiopulmonary bypass procedures, rheumatoid arthritis, systemic lupus erythematosus, thrombotic thrombocytopenic purpura, heparin-associated thrombosis, and organ transplant rejection comprising the step of treating a patient with an inhibitor of the PL scramblase activity PL scramblase.

The present invention is also a method for diagnosing individuals with reduced or elevated capacity for platelet-promoted or erythrocyte-promoted fibrin clot activity by quantitating the level of cellular expression of PL scramblase in the individual. This method may be performed by using an antibody to PL scramblase in an immunoblot, ELISA, or fluorescence flow cytometric method. The method may also be performed using oligonucleotides derived by PL scramblase cDNA in the polymerase chain reaction. In another embodiment, the method may be performed by isolating PL scramblase from a whole blood sample, measuring the amount of PL scramblase isolated and comparing the measurement with a control sample.

One may wish to use the protein preparation of the present invention as a hemostatic agent by topically applying the protein preparation to a wound area in a freely bleeding patient.

EXAMPLES

In the Examples below, we identify the cellular component that functions to mediate the $Ca^{2+}$-dependent reorganization of plasma membrane phospholipids, we identify the essential structural elements of this protein that are required for its phospholipid transporting function, and we describe methods for inhibiting or accelerating egress of PS to the surface of activated, injured, or apoptotic cells.

Example 1

Purification, Sequencing and Molecular Cloning of Human PL Scramblase

A. Summary

The rapid movement of phospholipids (PL) between plasma membrane leaflets is thought to play a key role in expression of platelet procoagulant activity and in clearance of injured or apoptotic cells. U.S. Ser. No. 08/790,186, upon which this application claims priority, discloses isolation of a ~37 kDa protein in erythrocyte membrane that mediates $Ca^{2+}$-dependent movement of PL between membrane leaflets, similar to that observed upon elevation of $Ca^{2+}$ in the cytosol [F. Bassé, et al. *J. Biol. Chem.* 271:17205–17210, 1996]. Based on internal peptide sequence obtained from this protein, a 1,445 bp cDNA was cloned from a K562 cDNA library. The deduced protein is a proline-rich, type II plasma membrane protein with a single transmembrane segment near the C-terminus. Antibody against the deduced C-terminal peptide was found to precipitate the ~37 kDa red blood cell protein and absorb PL scramblase activity, confirming the identity of the cloned cDNA to erythrocyte PL scramblase. $Ca^{2+}$-dependent PL scramblase activity was also demonstrated in recombinant protein expressed from plasmid containing the cDNA. Quantitative immunoblotting revealed an approximately 10-fold higher abundance of PL scramblase in platelet (~$10^4$ molecules per cell) than in erythrocyte. (~$10^3$ molecules/cell), consistent with apparent increased PL scramblase activity of the platelet plasma membrane. PL scramblase mRNA was found in a variety of hematologic and non-hematologic cells and tissues, suggesting that this protein functions in all cells.

B. Experimental Procedures

All experimental procedures and abbreviations are as set out in U.S. Ser. No. 08/790,186, unless otherwise noted anti-306–318, affinity purified rabbit antibody (IgG fraction) against peptide [C]ESTGSQEQKSGVW (SEQ ID NO:5); EST, expressed sequence tag; IPTG, isopropyl-β-D-thiogalactopyranoside; MBP, maltose binding protein;

Materials. Egg yolk phosphatidylcholine (PC), brain phosphatidylserine (PS), 1-palmitoyl 2-oleoyl phosphatidic acid, 1-oleoyl-2-[6(7-nitrobenz-2-oxa-1,3-diazol-4-yl)amino]caproyl-sn-glycero-3-phosphocholine (NBD-PC) and 1-oleoyl-2-[6(7-nitrobenz-2-oxa-1,3-diazol-4-yl)amino]caproyl-sn-glycero-3-phosphoserine (NBD-PS) were obtained from Avanti Polar Lipids. Expressed sequence tag (EST) clone with GenBank accession number gb AA143025 was obtained through American Type Culture Collection (ATCC962235). All restriction enzymes and amylose resin were from New England BioLabs, Inc. Klentaq polymerase was from Clontech Laboratories, wheat germ agglutinin Sepharose from Sigma, IPTG from Eastman Kodak, factor Xa from Haematologic Technologies, and Bio-Beads SM-2 were from BioRad. N-octyl-β-D-glucopyranoside (OG) and Glu-Gly-Arg chloromethyl ketone were from Calbiochem. Sodium dithionite ($Na_2S_2O_4$, Sigma) was freshly dissolved in 1 M Tris pH 10 at a concentration of 1 M. N-Octyl-β-D-glucopyranoside (OG) was purchased from Calbiochem. Sodium dithionite ($Na_2S_2O_4$, Sigma) was freshly dissolved in 1 M Tris pH 10 at a concentration of 1 M.

PL Scramblase isolation. Human PL scramblase protein and cDNA was obtained as described in Ser. No. 08/790, 186.

Cloning of PL scramblase into pMAL-C2 expression vector. In order to express PL scramblase as a fusion protein with maltose binding protein (MBP), cDNA encoding PL scramblase was cloned into pMAL-C2 (New England BioLabs). PCR was performed on a full-length clone using the primerss⁵'TCA GAA TTC GGA TCC ATG GAC AAA CAA AAC TCA CAG ATG³'(SEQ ID NO:6) with an EcoR1 site before the ATG start codon and ⁵'GCT TGC CTG CAG GTC GAC CTA CCA CAC TCC TGA TTT TTG TTC C³ (SEQ ID NO:7) with a SaiII site after the stop codon. KlenTaq polymerase (Clontech) was used to ensure high fidelity amplification. The PCR product was digested with EcoR1 and SaiII and isolated by electrophoresis on 1% low melting agarose gel and purification with Wizard kit (Promega). The amplified cDNA was cloned into pMAL-C2 vector digested with EcoRI and SalI, immediately 3' of MBP. This construct was amplified in *E. coli* strain TB1, and sequence of the cDNA insert of plasmids from single colonies confirmed.

Expression and purification of PL scramblase-MBP fusion protein. Ten ml of *E. coli* TB1 transformed with PL scramblase cDNA-pMAL-C2 were used to inoculate 1 L of rich LB containing 2 mg/ml glucose, 100 μg/ml ampicillin, and the bacteria were allowed to grow for about 4 hours at 37° C. When $A_{600}$ reached ~0.5, IPTG was added to a final concentration of 0.3 mM. After 2 hours of incubation at 37° C., the cells were centrifuged at 4000×g for 20 minutes. The cell pellet was suspended in 50 ml of 20 mM Tris, 200 mM NaCl, 1 mM EDTA, 1 mM DTT, 1 mM PMSF (column buffer), and subjected to a freeze/thaw cycle. After sonication (3×30 seconds on ice) and centrifugation at 43,000×g for 1 hour, the supernatant was applied to 10 ml of amylose resin. The column was washed with 20 volumes of column buffer, and the scramblase-MBP fusion protein eluted with the same buffer containing 10 mM maltose. Digestion of MBP-PL scramblase protein with factor Xa was routinely performed at 1/100 (w/w) ratio of enzyme and monitored by SDS-PAGE. In addition to MBP, the product of this digest is the PL scramblase translation product containing the N-terminal extension Ile-Ser-Glu-Phe-Gly-Phe (codons −6 to −1).

Reconstitution of PL scramblase or scramblase fusion protein into proteoliposomes. Reconstitution and functional activity were performed essentially as previously described (F. Bassé, et al., *J. Biol. Chem.* 271:17205–17210, 1996; J. G. Stout, et al., *J. Clin. Invest.* 99:2232–2238, 1997). Briefly, a mixture of PC and PS (9:1 molar ratio) was dried under a stream of nitrogen and resuspended in 100 mM Tris, 100 mM KCl, 0.1 mM EGTA, pH 7.4 (Tris buffer). Protein samples to be reconstituted were added to the liposomes at a final lipid concentration of 4 mg/ml in the presence of 60 mM OG, and dialyzed overnight at 4° C. against 200 vol of Tris buffer containing 1 g/L Bio-Beads SM-2. To liberate PL scramblase from MBP, the proteoliposomes were incubated 3 h at room temperature in the presence of 1/40 (w/w) factor Xa. The digestion was terminated by addition of 100 $\mu$M Glu-Gly-Arg chloromethyl ketone. Completeness of the digest was monitored by SDS-PAGE. Following dialysis, the proteoliposomes were labeled in the outer leaflet by addition of 0.25 mol % fluorescent NBD-PC (in dimethyl sulfoxide, final solvent concentration 0.25%).

PL Scramblase activity. Scramblase activity was measured as previously described (F. Bassé, et al., supra, 1996; J. G. Stout, et al., supra, 1997 and in U.S. Ser. No. 08/790, 186). Routinely, proteoliposomes labeled with NBD-PC were incubated for 2 hours at 37° C. in Tris buffer in the presence or absence of 2 mM $CaCl_2$. Proteoliposomes were diluted 25-fold in Tris buffer containing 4 mM EGTA and transferred to a stirred fluorescence cuvet at 23° C. Initial fluorescence was recorded (SLM Aminco 8000 spectrof luorimeter; excitation at 470 nm, emission at 532 nm), 20 mM dithionite was added, and the fluorescence continuously monitored for a total of 120 seconds. The difference in non-quenchable fluorescence observed in presence vs. absence of $CaCl_2$ Was attributed to $Ca^{2+}$-induced change in NBD-PC located in the outer leaflet (F. Bassé, et al., supra, 1996; J. G. Stout, et al., supra, 1997; J. C. McIntyre and R.G. Sleight, *Biochemistry* 30:11819–11827, 1991). Ionized [$Ca^{2+}$] was calculated using FreeCal version 4.0 software (generously provided by Dr. Lawrence F. Brass, University of Pennsylvania, Philadelphia, Pa.).

Antibody against PL Scramblase C-terminal peptide.

The peptide CESTGSQEQKSGVW (SEQ ID NO:5), corresponding to amino acids 306–318 of the predicted open reading frame of PL scramblase with an added N-terminal cysteine, was synthesized and conjugated to keyhole limpet hemocyanin (Protein Core Facility, Blood Research Institute). Antiserum to this protein was raised in rabbit (Cocalico Biologicals, Inc.) and the IgG fraction isolated on Protein A Sepharose-CL4B (Sigma). Peptide-specific antibody was isolated by affinity chromatography on UltraLink Iodoacetyl beads (Pierce) to which peptide CESTG-SQEQKSGVW (SEQ ID NO:5) was conjugated. This affinity-purified antibody (anti-306–318) was used for immunoprecipitation and Western blotting of PL scramblase (below).

Immunoprecipitation of PL scramblase. PL scramblase purified from human erythrocytes was $^{125}$I-labeled with Iodogen (Pierce), free iodide removed by gel filtration, and the protein incubated (4° C., overnight) with either anti-306–318, or an identical quantity of pre-immune rabbit IgG (1 mg/ml in 150 mM NaCl, 10 mM MOPS, 50 mM OG, pH 7.4) or no IgG as control. The IgG was precipitated with protein A Sepharose, washed exhaustively, and protein bands resolved by 8–25% SDS-PAGE (Phast System, Pharmacia Biotech Inc.) under reducing conditions. Radioactive bands were visualized by autoradiography. In order to determine whether antibody to this peptide specifically removed the functional activity associated with the purified erythrocyte PL scramblase protein, the supernatant fractions remaining after immunoprecipitation were reconstituted in liposomes for activity measurements, performed as described above. For these experiments, unlabeled erythrocyte PL scramblase substituted for the $^{125}$I-labeled protein.

Western Blot Analysis. $2 \times 10^8$ washed platelets, $2 \times 10^8$ erythrocyte ghost membranes, 0.9 pmoles of purified recombinant PL scramblase (obtained by factor Xa digest of the PL scramblase-MBP fusion protein), or 0.3 pmoles of PL scramblase purified from human erythrocyte were each denatured by boiling in 40 $\mu$l sample buffer containing 10% SDS, 4% $\beta$-mercaptoethanol, and 1 mM EDTA, and protein bands resolved by SDS-PAGE. After transfer to nitrocellulose, the blocked membrane was incubated with 1 $\mu$g/ml of anti-306–318, and the blot developed with horseradish preoxidase-conjugated goat anti-rabbit IgG (Sigma) using Chemiluminescence Reagent (Dupont).

Protein Concentrations. Protein concentrations were estimated based upon optical density at 280 nm, using extinction coefficients ($M^{-1}cm^{-1}$) of 39,000 (PL scramblase), 64,500 (MBP), and 105,000 (PL scramblase-MBP fusion). PL scramblase contained in human platelet and erythrocyte membranes was estimated by quantitative immunoblotting of the detergent extracts, with reference to known quantities of purified MBP-PL scramblase fusion protein.

Northern Blot Analysis. Human multiple tissue northern blot and human cancer cell line multiple tissue northern blot membranes were obtained from Clontech. The blots were prehybridized with ExpressHyb (Clontech) at 68° C. for 30 minutes and hybridized with ExpressHyb containing 5 ng/ml $^{32}$P-labeled PL scramblase CDNA probe at 68° C. for 1 hour, then washed and exposed to X-ray film. After development, the blots were stripped and hybridized with $^{32}$P-labeled $\beta$-actin cDNA probe using identical conditions.

C. Results and Discussion

U.S. Ser. No. 08/790,186 describes the initial purification of PL scramblase from human erthyocyte membrane and analysis of cyanogen bromide fragments. The fragments were used to obtain an entire PL scramblase DNA alone (FIG. 1).

FIG. 1A illustrates the cDNA and deduced amino acid sequence of human PL scramblase. The deduced amino acid sequence of the predicted open reading frame is shown under the nucleotide sequence. The 32 residues of peptide sequence that were obtained from cyanogen bromide digest of purified erythrocyte PL scramblase are indicated by single underline. Also indicated are the residues comprising a predicted inside-to-outside transmembrane domain (Ala291–Gly309; double underline) and protein kinase C phosphorylation site (Thr161; asterisk). See Experimental Procedures for details.

Analysis of the cDNA-derived protein sequence (Tmpred program, ISREC server, Univ. of Lausanne, Epalinges, Switzerland) revealed a strongly-preferred (p<0.01) inside-to-outside orientation of the predicted 19 residue transmembrane helix, consistent with a type II plasma membrane protein. Most of the polypeptide (residues 1–290) thereby extends from the cytoplasmic membrane leaflet, leaving a short exoplasmic tail (residues 310–318). The predicted orientation of this protein is consistent with the anticipated topology of PL S scramblase in the erythrocyte membrane, where lipid-mobilizing function is responsive to [$Ca^{2+}$] only at the endofacial surface of the membrane (P. Williamson, et al., *Biochemistry* 31:6355–6360, 1992; E. F. Smeets, et al., *Biochim. Biophys. Acta Bio-Membr.* 1195:281–286, 1994; F. Bassé, et al., supra, 1996; J. G. Stout, et al., supra, 1997; P.

Williamson, et al., *Biochemistry* 34:10448–10455, 1995; D. L. Bratton, *J. Biol. Chem.* 269:22517–22523, 1994).

In order to confirm that the cDNA we cloned from the K562 cDNA library actually encodes the same protein purified as PL scramblase from human erythrocyte membrane, we raised a rabbit antibody against the deduced C-terminus predicted from the open reading frame of the cloned cDNA (codons 306–318).

FIG. 2 illustrates immunoprecipitation of erythrocyte PL scramblase. PL scramblase purified from human erythrocytes was precipitated with either anti-306–318 IgG (bar 1), or with pre-immune rabbit IgG (bar 2) and protein remaining in the supernatant reconstituted into liposomes for measurement of residual PL scramblase activity. Data normalized to PL scramblase activity measured for identical controls omitting antibody (100%; bar 3). Error bars denote mean±SD (n=4).

As shown in FIG. 2, this antibody precipitated the ~37 kDa red cell protein we tentatively identified as PL scramblase, and also absorbed the functional activity detected in this isolated erythrocyte membrane protein fraction. We often observed the partial proteolysis of 37 kDa PL scramblase to a polypeptide of ~30 kDa. The apparent susceptibility of this protein to proteolytic degradation may account for the reported rapid loss of activity observed in earlier attempts to purify PL scramblase from platelet (P. Comfurius, et al., *Biochemistry* 35:7631–7634, 1996).

Expression and membrane reconstitution of recombinant PL scramblase. Recombinant PL scramblase was expressed in *E. coli* as fusion protein with MBP, purified by amylose affinity chromatography, and incorporated into PC/PS liposomes for assay of PL scramblase activity. When incorporated into liposomes, the recombinant protein mediated a $Ca^{2+}$-dependent transbilayer movement of NBD-PC mimicking the activity of PL scramblase isolated from erythrocyte. PL scramblase activity was observed both for the chimeric MBP-PL scramblase fusion protein, and for recombinant PL scramblase liberated from MBP through proteolytic digestion with factor Xa (FIG. 3).

Figure 3:
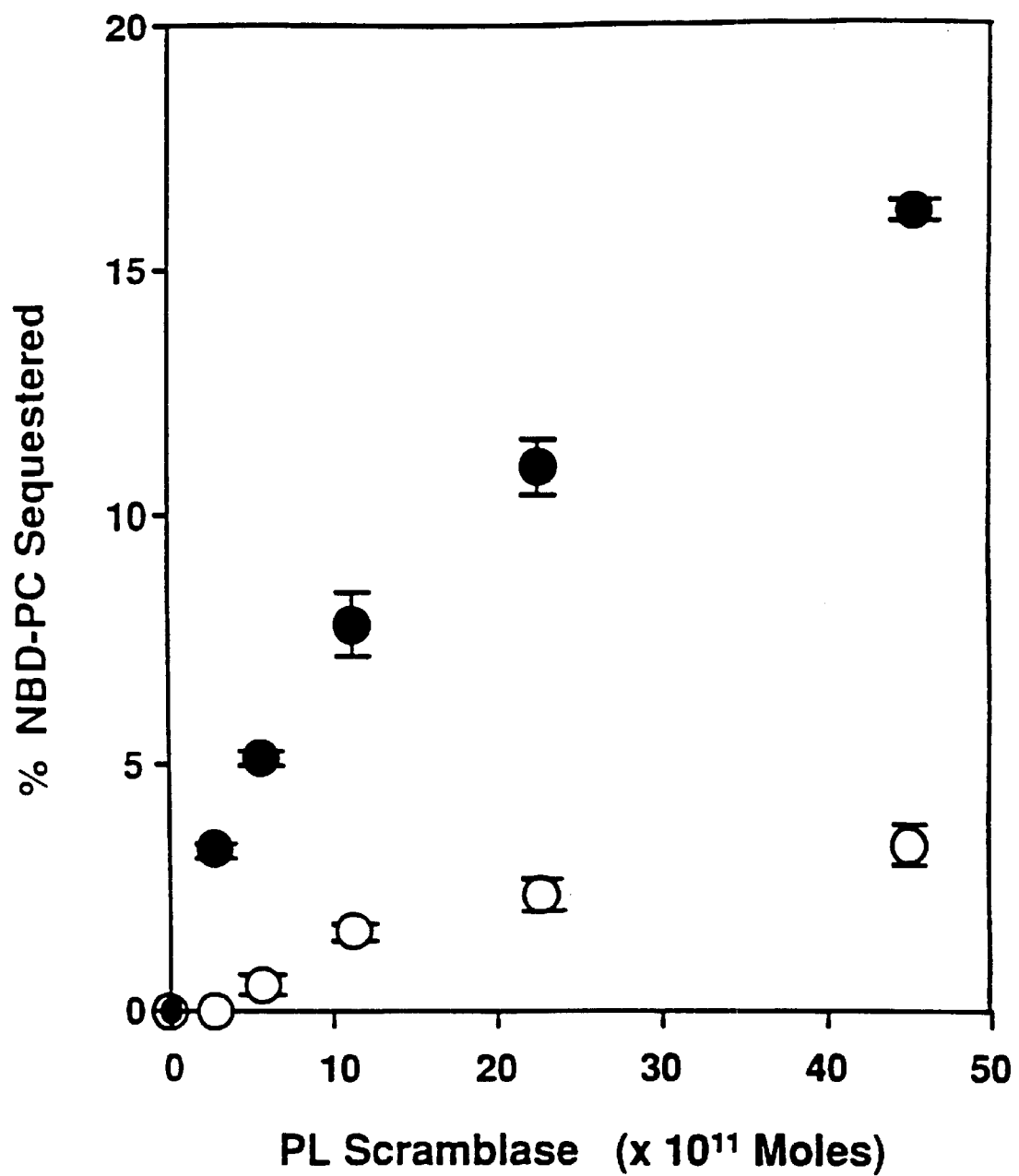
FIG. 3 is a graph of an activity assay of recombinant PL scramblase.

FIG. 3 depicts an activity assay of recombinant PL scramblase. Purified PL scramblase-MBP fusion protein ($0-43\times10^{-11}$ moles; abscissa) was reconstituted into liposomes (1 µmole total PL) and MBP proteolytically removed by incubation with factor Xa in presence of 0.1 mM EGTA. After digest to release MBP, the proteoliposomes were recovered for determination of PL scramblase activity, measured in the absence (o) or presence (●) of 2 mM $CaCl_2$ as described in Experimental Procedures. Data are corrected for non-specific transbilayer migration of NBD-PC probe in identically-matched control liposomes containing either MBP or no added protein (<2% NBD-PC sequestered; not shown). Error bars denote mean±SD (n=3). Data of single experiment, representative of two so performed. Similar results were also obtained for proteoliposomes containing intact PL scramblase-MBP fusion protein, omitting the factor Xa digest (not shown).

By contrast, no such activity was observed for control protein consisting of the pMAL-C2 translation product MBP lacking the PL scramblase cDNA insert. The specific PL mobilizing activity of recombinant PL scramblase expressed and purified from *E. coli* was approximately 50% of that observed for the endogenous protein purified from the erythrocyte membrane, which is likely due to incomplete folding of the recombinant protein. Half-maximal $[Ca^{2+}]$ required for activation was approximately 100–200 µM for recombinant protein purified from *E. coli* versus ~40 µM for the erythrocyte-derived protein, raising the possibility that altered folding or an unknown post-translational modification in mammalian cells affects the putative $Ca^{2+}$ binding site (F. Bassé, et al., supra, 1996; J. G. Stout, et al., supra, 1997). In addition to activation by $Ca^{2+}$, the transbilayer migration of PL in erythrocytes is accelerated upon acidification of the inside leaflet to pH<6.0 (in absence of $Ca^{2+}$), a response that is also observed in proteoliposomes containing PL scramblase purified from erythrocyte membranes (J. G. Stout, et al., supra, 1997). A similar acid-dependent activation of PL mobilizing function was also exhibited by proteoliposomes incorporating recombinant PL scramblase purified from *E. coli*.

Figure 4:
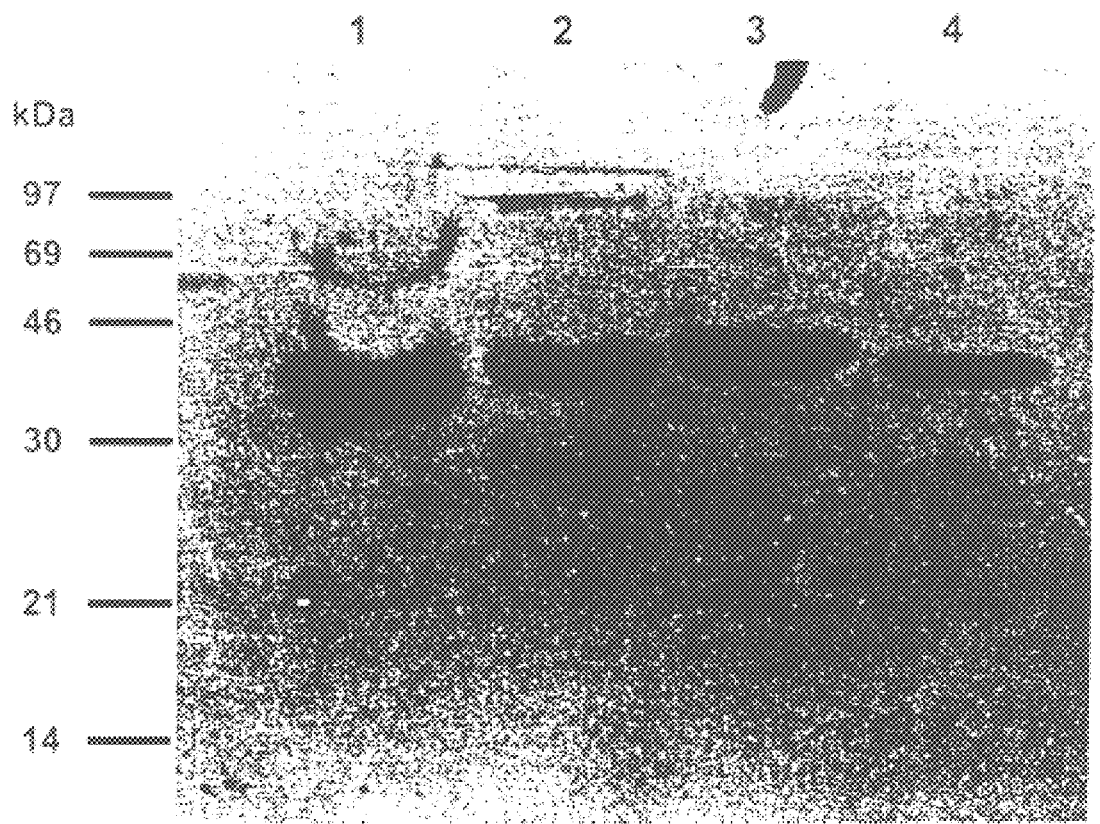
FIG. 4 is an immunoblot of PL scramblase in human erythrocytes and platelets.

Platelet PL Scramblase. In addition to the presumed role of PL scramblase in PS exposure following cell injury and upon repeated sickling of SS hemoglobin red cells, the capacity of activated platelets to rapidly mobilize aminophospholipids across the plasma membrane is thought to play a central role in the initiation of thrombin generation required for plasma clotting (R. F. A. Zwaal and A. J. Schroit, *Blood* 89:1121–1132, 1997). Whereas incubation with $Ca^{2+}$ ionophore causes a marked acceleration in transbilayer movement of plasma membrane PL in both platelets and erythrocytes, the apparent rate of transbilayer PL migration in platelet exceeds that in erythrocyte by approximately 10-fold, implying either a higher abundance of PL scramblase, or the action of another component in platelet with enhanced PL scrambling function (J. C. Sulpice, et al., *J. Biol. Chem.* 269:6347–6354; 1994; J. C. Sulpice, et al., *Biochemistry* 35:13345–13352, 1996). Zwaal and associates recently reported evidence for the existence of protein(s) in platelet with functional properties similar to that of PL scramblase we isolated from erythrocyte (F. Bassé, et al., supra, 1996; J. G. Stout, et al., supra, 1997; P. Comfurius,et al., supra, 1996). In order to determine whether the protein we now identify in the erythrocyte membrane is also found in platelets, we probed platelets with antibody against PL scramblase residues 306–318. FIG. 4 illustrates immunoblotting of PL scramblase in human erythrocytes and platelets. $2\times10^8$ platelets (lane 1), and ghost membranes from $2\times10^8$ erythrocytes (lane 2), were separated by SDS-PAGE, transferred to nitrocellulose and Western blotted with anti-306–318 antibody as described in Experimental Procedures. Lane 3 contains 0.9 pmoles of factor Xa cleaved recombinant PL scramblase and lane 4 contains 0.3 pmoles of PL scramblase purified from erythrocytes. Data of single experiment representative of three so performed.

As shown in FIG. 4, this antibody blotted a single protein in platelet with similar mobility to the ~37 kDa PL scramblase in erythrocyte. Based on quantitative immunoblotting with anti-306–318, we estimate approximately $10^4$ molecules/cell in platelet versus $10^3$ molecules/cell in erythrocyte, consistent with the increased PL scramblase activity and procoagulant function observed for human platelets versus erythrocytes.

Tissue Distribution. In addition to platelet and red blood cell, PL scramblase activity has been observed in many other cells, and this $Ca^{2+}$-induced response is thought to be central to the rapid movement of PS and phosphatidylethanolamine from inner plasma membrane leaflet to the surface of perturbed endothelium, and a variety of injured and apoptotic cells (R. F. A. Zwaal and A. J. Schroit, supra, 1997). The resulting exposure of PS at the cell surface is thought to play a key role in removal of such cells by the reticuloendothelial system, in addition to activation of both the plasma complement and coagulation systems (R. H. Wang, et al.,*J. Clin. Invest.* 92:1326–1335, 1993; V. A. Fadok, et al., *J. Immunol.* 148:2207–2216, 1992; R. F. A. Zwaal and A. J.

Schroit, supra, 1997). Whereas the molecular mechanism(s) in each circumstance remains unresolved, evidence for a specific platelet membrane protein functioning to accelerate migration of PL between membrane leaflets at increased cytosolic [$Ca^{2+}$] has been reported (P. Comfurius, et al., supra, 1996), similar to the proposed role of PL scramblase in red blood cells (F. Bassé, et al., supra, 1996; J. G. Stout, et al., supra, 1997). It was thus of interest to determine whether mRNA for this protein is expressed in nucleated cells where PL scramblase-like activity has been observed.

Northern blotting with PL scramblase cDNA revealed transcripts of ~1.6 and ~2.6 kb in all tissues and cell lines tested. Some tissue-to-tissue and cell line variability in the relative abundance of these two transcripts is apparent, the significance of which remains to be determined. Also notable was markedly reduced expression in HL-60 and the lymphoma lines Raji and MOLT-4 whereas abundant message was detected in spleen, thymus, and peripheral leukocytes. In addition to the transformed cell lines shown, mRNA for PL scramblase was also confirmed in human umbilical vein endothelial cells. Whereas these data imply that the same protein identified as mediating accelerated transbilayer flip-flop of the erythrocyte membrane PL also plays a similar role in the plasma membrane of platelets, leukocytes and other cells, actual confirmation for this role of PL scramblase awaits analysis of a cell line that is selectively deficient in this protein. In Scott syndrome, a bleeding disorder related to an inherited deficiency of plasma membrane PL scramblase function, erythrocytes deficient in PL scramblase activity were found to contain normal amounts of the PL scramblase protein (J. G. Stout, et al., supra, 1997) and unpublished data). Furthermore, despite the apparent deficiency in Scott syndrome cells of endogenous PL scramblase function, when PL scramblase protein from these cells was purified and reconstituted in proteoliposomes containing exogenous PL, it exhibited normal $Ca^{2+}$-dependent PL-mobilizing activity (J. G. Stout, et al., supra, 1997). This suggests that in addition to the known regulation by intracellular [$Ca^{2+}$], the activity of PL scramblase in the plasma membrane is regulated by other as yet unidentified membrane or cytoplasmic component (s).

Example 2

Cloning of Murine PL Sscramblase and Identity of a Conserved Motif in Phospholipid Scramblase that is Required for Accelerated Transbilayer Movement of Membrane Phospholipids by $Ca^{2+}$ A. Summary Accelerated transbilayer movement of plasma membrane phospholipids (PL) upon elevation of $Ca^{2+}$ in the cytosol plays a central role in the initiation of plasma clotting and in phagocytic clearance of injured or apoptotic cells. We recently identified a human erythrocyte membrane protein that induces rapid transbilayer movement of PL at elevated $Ca^{2+}$, and presented evidence that this PL scramblase is expressed in a variety of other cells and tissues where transbilayer movement of plasma membrane PL is promoted by intracellular $Ca^{2+}$ (Q. Zhou, et al., *J. Biol. Chem.* 272:18240–18244, 1997). We have now cloned murine PL scramblase for comparison to the human polypeptide (FIG. 1B): Both human and murine PL scramblase are acidic proteins (pI=4.9) with a predicted inside-outside (type 2) transmembrane segment at the carboxyl-terminus (FIG. 5). Whereas human PL scramblase (318 AA) terminates in a short exoplasmic tail, murine PL scramblase (307 AA) terminates in the predicted membrane-inserted segment. The aligned polypeptide sequences reveal 65% overall identity, including near identity through 12 residues of an apparent $Ca^{2+}$ binding motif (D[A/S]DNFGIQFPLD) spanning residues 273–284 (human, SEQ ID NO:2) and 271–282 (murine, SEQ ID NO:4), respectively (FIG. 5). This conserved sequence in the cytoplasmic domain of PL scramblase shows similarity to $Ca^{2+}$-binding loop motifs previously identified in known EF-hand structures. Recombinant murine and human PL scramblase were each expressed in *E. coli* and incorporated into proteoliposomes. Measurement of transbilayer movement of NBD-labeled PL confirmed that both proteins catalyzed $Ca^{2+}$-dependent PL flip/flop similar to that observed for the action of $Ca^{2+}$ at the cytoplasmic face of plasma membranes. Mutation of residues within the putative EF hand loop of human PL scramblase resulted in loss of its PL mobilizing function, suggesting that these residues directly participate in the $Ca^{2+}$ induced active conformation of the polypeptide.

B. Experimental Procedures

Abbreviations used: PL, phospholipids(s); PC, phosphatidylcholine; PS, phosphatidylserine; NBD-PC, 1-oleoyl-2-[6 (7-nitrobenz-2-oxa-1,3-diazol-4-yl)amino]caproyl-sn-glycero-3-phosphocholine; EST, expressed sequence tag; MBP, maltose binding protein; PAGE, polyacrylamide gel electrophoresis; bp, base pair(s); PCR; polymerase-chain reaction.

Materials: Mouse fibroblast 5'-stretch plus cDNA library and KlenTaq polymerase were obtained from CLONTECH Laboratories. Expressed sequence Tag (EST) clone with GenBank™ accession number gb AA110551 was from American Type Culture Collection (ATCC 977052). $\alpha$-$^{32}$P-dCTP was purchased from Dupont. Random Primed DNA Labeling Kit was from Boehringer Mannheim. Hybond-N Nylon membrane was from Amersham. Expression vector pMAL-C2, amylose resin and all restriction enzymes were from New England Biolabs. Wizard Kit was from Promega. Qiagen Lambda Kit was from Qiagen. Egg yolk phosphatidylcholine (PC), brain phosphatidylserine (PS) and 1-oleoyl-2-[6(7-nitrobenz-2-oxa-1,3-diazol-4-yl)amino] caproyl-sn-glycero-3-phosphocholine (NBD-PC) were obtained from Avanti Polar Lipids. Factor Xa was from Haematologic Technologies, and Bio-Beads SM-2 were from BioRad. N-octyl-β-D-glucopyranoside and Glu-Gly-Arg chloromethyl ketone were from Calbiochem. Sodium dithionite (Sigma) was freshly dissolved in 1M Tris, pH 10, at a concentration of 1 M.

Labeling of DNA Probe: The DNA insert of EST clone gb AA110551 was released by digestion with EcoRI and ApalI and purified by Wizard Kit. Four micrograms of purified DNA were labeled with 1 mCi of $\alpha$-$^{32}$P-dCTP. The specific radioactivity of the probe was $3.9 \times 10^8$ dpm/$\mu$g DNA.

Isolation of Mouse PL Scramblase CDNA by Plaque Hybridization: *E. coli* strain Y1090 or was transformed by mouse fibroblast cDNA library ($6 \times 10^5$ pfu) and poured onto 30 plates (15 cm diameter, 20,000 pfu per plate). Plaques were lifted onto Hybond-N Nylon membranes. After denaturation, neutralization and UV-cross linking, the membranes were first prehybridized in a solution composed of 5×Denhardt, 5×SSC, 1% SDS, and 200 $\mu$g/ml herring sperm DNA for 3 hours at 68° C., and then hybridized in the same solution containing 5 ng/ml $^{32}$P-labeled probe for 16 hours at 68° C. The membranes were washed once with 2×SSC, 0.1% SDS, then three times with 0.1×SSC, 0.1% SDS for 20 minutes at 65° C., and exposed to X-ray film. Secondary plaque lifts and hybridization were carried out on 8 positive plaques at a density of about 100 plaques/plate. Single positive and well isolated plaques were picked and amplified. λDNA was purified with Qiagen Lambda Maxi Kit.

DNA Sequencing. DNA was sequenced on an ABI DNA Sequencer Model 373 Stretch (Applied Biosystems) using PRISM Ready Reaction DyeDeoxy Terminator Cycle Sequencing Kit (Perkin Elmer).

Cloning of Mouse PL Scramblase into pMAL-C2 Expression Vector. In order to express mouse PL scramblase as a fusion protein with maltose binding protein (MBP), cDNA encoding mouse PL scramblase was cloned into pMAL-C2 expression vector. PCR was performed on a mouse scramblase clone using the primers 5'TCA GAA TTC GGA TCC ATG GAG GCT CCT CGC TCA GGA AC3'(SEQ ID NO:8) with an EcoRI site before the ATG start codon and 5'GCT TGC CTG CAG GTC GAC CTA CAC ACA GCC TTC AAA AAA CAT G3'(SEQ ID NO:9) with a SalI site after the stop codon. KlenTaq polymerase was used to ensure high fidelity amplification. The PCR product was digested with EcoRI and SalI, isolated by electrophoresis, and cloned into pMAL-C2 immediately 3' of MBP. E. coli strain TB1 was transformed, and sequence of the CDNA insert of plasmid from a single colony was confirmed.

Expression and Purification of Mouse PL Scramblase-MBP Fusion Protein: Mouse PL scramblase was expressed as fusion protein with MBP in E. coli TB1 and purified on amylose resin as previously described for human PL scramblase (Q. Zhou, et al., J. Biol. Chem. 272:18240–18244, 1997). The purified fusion protein was centrifuged at 106,000×g for 1 hour at 4° C. to remove aggregated protein.

Reconstitution and Functional Activity of PL Scramblase: Reconstitution, removal of MBP, and functional assay of PL scramblase were performed as previously described (F. Bassé, et al., J. Biol. Chem. 271:17205–17210, 1996; Q. Zhou, et al., supra, 1997; J. G. Stout, et al., J. Clin. Invest. 99:2232–2238, 1997). Routinely, 420 pmoles of protein were reconstituted with 1 $\mu$mol of PL. To remove MBP, proteoliposomes were incubated 3 hours at room temperature with 1/40 (w/w) factor Xa. The digest was terminated by addition of 100 $\mu$M Glu-Gly-Arg chloromethyl ketone. Proteoliposomes labeled with NBD-PC were incubated for 2 hours at 37° C. in Tris buffer in the presence or absence of $CaCl_2$ as indicated in figure legends and diluted 25-fold in Tris buffer containing 4 mM EGTA. Initial fluorescence was recorded (SLM Aminco 8000 spectrofluorimeter; excitation at 470 nm, emission at 532 nm), 20 mM dithionite was added, and the fluorescence was continuously monitored for a total of 120 seconds. Scramblase activity was calculated according to the difference in non-quenchable fluorescence observed in presence vs absence of $CaCl_2$. Ionized $[Ca^{2+}]$ was calculated using FreeCal version 4.0 software (generously provided by Dr. Lawrence F. Brass, University of Pennsylvania, Philadelphia, Pa.).

Protein Concentrations: Protein concentrations were estimated based upon optical density at 280 nm, using extinction coefficients ($M^{-1}cm^{-1}$) of 39,000 (PL scramblase), 64,500 (MBP), and 105,000 (PL scramblase-MBP fusion protein).

Mutagenesis of PL Scramblase: Human PL scramblase amino acid residues in EF-hand $Ca^{2+}$-binding motif at positions of $Asp^{273}$, $Asp^{275}$, $Phe^{277}$, $Ile^{279}$, $Phe^{281}$ and $Asp^{284}$ were mutated to Ala with oligonucleotide-directed mutagenesis by two rounds of PCR. PL scramblase-pMAL-C2 was selected as template, and the first round of PCR was performed with pairs of a complementary oligonucleotide primer containing the point mutation plus a primer complementary to a site near the ATG initial codon or TAG stop codon. PCR products were purified by Wizard kit. Full length mutated PL scramblase cDNA was obtained by overlapping PCR and cloned back into pMAL-C2 vector. After confirmation of correct DNA sequence the mutants were recombinantly expressed in E. coli as described above and analyzed by SDS-PAGE.

C. Results and Discussion

Isolation of cDNA of Mouse PL Scramblase. Murine EST clones in GenBank containing putative PL scramblase sequence were identified by a Blast homology search using the human PL scramblase cDNA. Among several clones exhibiting significant homology, a 403 bp Stratagene mouse kidney clone (gb accession number AA110551) with 79% nucleotide sequence identity to human PL scramblase was selected and this clone was used to probe a mouse fibroblast cDNA library. Eight positive clones were identified after two rounds of plaque hybridization. Two of the eight clones were sequenced yielding 1354 bp and 1529 bp, respectively. Alignment revealed 1261 bp of overlapping sequence that spanned an open reading frame of 921 bp and specified a total of 1622 bp of unique cDNA sequence (SEQ ID NO:3).

SEQ ID NO:4 represents the open reading frame of the translated sequence of SEQ ID NO:3 (see FIG. 1B). The deduced mouse PL scramblase cDNA encodes a 307 residue protein with a molecular weight of 33.9 kDa and a theoretical pI=4.9, similar to values obtained for the human protein (318 residues, 35.1 kDa; pI=4.9; ref. (Q. Zhou, et al., supra, 1997). The overall identity of the mouse and human PL scramblase is 64.8%, with the most divergent sequence generally contained in the N-terminal portion of the polypeptide (FIG. 5). FIG. 5 depicts the alignment of protein sequences of mouse and human PL scramblase. Alignment between mouse (MUR) and human (HUM) PL scramblase was performed by FASTA program using the Smith-Waterman algorithm. (W. R. Pearson and D. J. Lipman, Proc. Natl. Acad. Sci. USA 85:2444–2448, 1988) Sequence of human PL scramblase is contained in GenBank™ accession number AF008445. Amino acid identities (:) or similarities (.) between the two sequences are indicated. Also indicated are the residues comprising a predicted inside-out transmembrane domain (MUR 289–307, HUM 291–309; double underline), and the 12 residues of the acidic loop of a putative EF-hand (MUR 271–282, HUM 273–284; single underline).

In both proteins, a single 19 residue transmembrane helix is predicted at the carboxyl terminus, exhibiting a strongly preferred inside-to-outside orientation. Whereas the mouse protein terminates immediately after this conserved transmembrane helix, the human PL scramblase contains an additional nine residues, implying that the short exoplasmic peptide in human PL scramblase is non-essential to function. Homology motifs conserved in both proteins include a potential site for protein kinase C phosphorylation ($Thr^{159}$ in mouse, $Thr^{161}$ in human) and a potential $Ca^{2+}$-binding EF-hand loop motif adjacent to the transmembrane helix (residue $Asp^{271}$ to $Asp^{282}$ in mouse and residues $Asp^{273}$ to $Asp^{284}$ in human). The cytoplasmic orientation of this protein and the proximity of this putative $Ca^{2+}$-binding domain to the segment of polypeptide that is inserted into the plasma membrane are consistent with the proposed activity of this protein in situ, where $Ca^{2+}$ acting directly at the endofacial membrane surface is known to initiate the rapid transbilayer movement of plasma membrane PL (P. Williamson, et al., Biochemistry 31:6355–6360, 1992; R. F. A. Zwaal, and A. J. Schroit, Blood 89:1121–1132, 1997; F. Bassé, et al., J. Biol. Chem. 271:17205–17210, 1996; D. L. Bratton, J. Biol. Chem. 269:22517–22523, 1994; B. Verhoven, et al., Biochim. Biophys. Acta 1104:15–23, 1992).

Functional Activity of Recombinant Mouse PL Scramblase. In order to confirm that the cDNA identified as mouse PL scramblase encodes a protein of similar function to that identified in human, the human and mouse proteins were each expressed in *E. coli*, purified, and reconstituted in proteoliposomes for measurement of PL mobilizing activity. Mouse or human PL scramblase-MBP fusion protein (420 pmoles) was reconstituted into PC/PS liposomes (1 μmol total PL), respectively, MBP was removed by digestion of the proteoliposomes with factor Xa, and PL scramblase activity was determined as described under "Experimental Procedures" and plotted as a function of external free [$Ca^{2+}$]. The results of this experiment indicate that recombinant mouse PL scramblase mediated a $Ca^{2+}$-dependent transbilayer movement of membrane PL with a specific activity and affinity for $Ca^{2+}$ indistinguishable from that observed for the recombinant human protein.

Mutational Analysis of a Putative Conserved EF-Hand Motif. As noted above, the deduced protein sequence of mouse and human PL scramblase reveals an extensive segment of highly conserved sequence extending through residue $Glu^{306}$ (in human; corresponding to $Glu^{304}$ in mouse; FIG. 5). The predicted secondary structure through this portion of the protein reveals that it contains two short alpha-helical segments near the C-terminus that are separated by a 12-residue acidic loop. In both proteins (human and mouse), the C-terminal alpha helix represents a predicted transmembrane segment with a strongly-preferred inside-to-outside orientation, whereas sequence contained within the adjacent 12-residue acidic loop conforms in-part to a consensus sequence that is characteristic of an EF-hand $Ca^{2+}$-binding loop motif (S. Nakayama and R. H. Kretsinger, Annu. Rev. Biophys. Biomol. Struct. 23:473–507, 1994). In this motif, residues in positions 1, 3, 5, 7, 9 and 12 of the loop contribute to octahedral coordination of the $Ca^{2+}$ ion, with the residues in position 1 [Asp], 3 [Asp, Asn, or Ser] and 12 [Asp or Glu] being those most highly conserved.

In order to gain insight into whether this segment of the protein might be directly involved in the $Ca^{2+}$-dependent reorganization of membrane PL mediated by PL scramblase, we expressed mutant human PL scramblase with Ala substitutions at positions corresponding to residues 1 ($Asp^{273}$), 3 ($Asp^{275}$), 5 ($Phe^{277}$), 7 ($Ile^{279}$), 9 ($Phe^{281}$), and 12 ($Asp^{284}$) of this putative 12 residue EF-hand loop.

Figure 6:
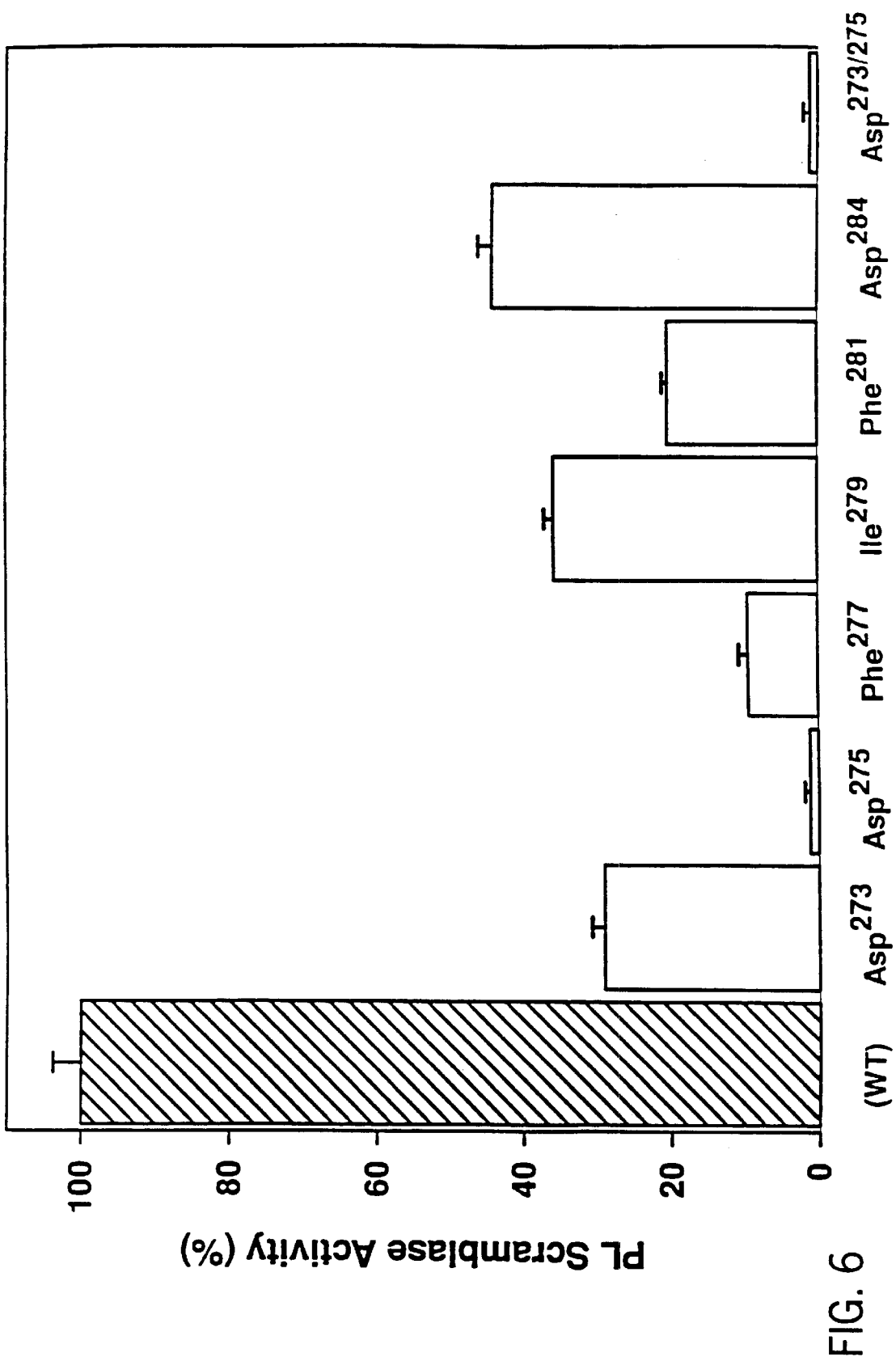
FIG. 6 is a bar graph of PL scramblase activity as a function of mutational analysis of a putative EF hand loop motif contained in human PL scramblase.

FIG. 6 illustrates PL scramblase activity as a function of mutational analysis of putative EF hand loop motif contained in human PL scramblase. Wild-type (WT) and mutant constructs of human PL scramblase were expressed as fusion proteins with MBP in *E. coli*, purified, and reconstituted in proteoliposomes. After release of MBP by incubation with factor Xa, PL scramblase activity was assessed (see "Experimental Procedures"). For each mutant construct, the residues in human PL scramblase that were replaced by Ala are indicated on the abscissa. PL scramblase activity (ordinate) was measured in presence of 2 mM $CaCl_2$, and in each case was normalized to the activity of WT human PL scramblase (11.76±0.44% of total NBD-PC flipped), with correction for the non-specific transbilayer movement of NBD-PC (0.20±0.08% of total NBD-PC flipped) measured in PL vesicles lacking added protein. Error bars indicate mean±SD of three independent measurements performed with each mutant construct. FIG. 6 illustrates the data of single experiment, representative of two separate experiments so performed.

Figure 7:
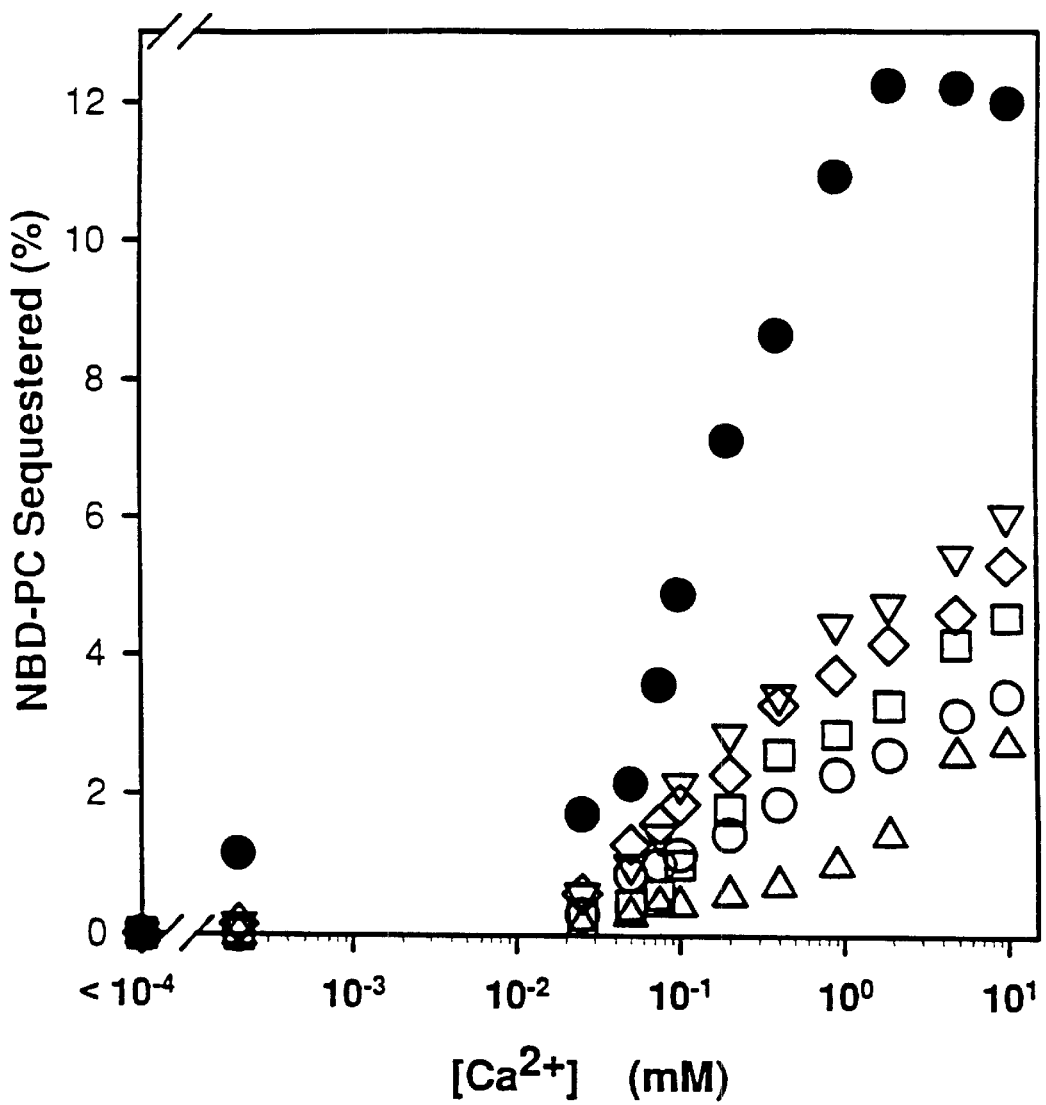
FIG. 7 graphs the $Ca^{2+}$ dependence of mutant human PL scramblase.

As illustrated by FIG. 6, Ala substitution at any of these positions reduced PL scramblase function, with mutation at $Asp^{275}$ resulting in complete inactivation of the $Ca^{2+}$-dependent response. In those mutant polypeptides showing partial retention of activity, reduced response to $Ca^{2+}$ was related in-part to an apparent reduction in avidity for $Ca^{2+}$ (FIG. 7). FIG. 7 illustrates the $Ca^{2+}$-dependence of mutant human PL scramblase. PL scramblase activity of wild-type (WT) and selected mutant constructs of FIG. 6 was determined as described in "Experimental Procedures" and plotted as a function of external free [$Ca^{2+}$]: WT(●); $Asp^{273}$(□); $Phe^{277}$(△); $Ile^{279}$ (◇); $Phe^{281}$(○); $Asp^{284}$(▽). The data are corrected for non-specific transbilayer migration of NBD-PC in the absence of free [$Ca^{2+}$]. Data of single experiment. The results described in FIG. 7 suggest that residues contained in the putative EF-hand loop spanning $Asp^{273}$–$Asp^{284}$ are critical to the function of PL scramblase, presumably for coordination of $Ca^{2+}$ as required to induce the PL transporting state of the protein. It remains to be determined what conformational changes are induced in the polypeptide in the presence of $Ca^{2+}$, including potential reorientation of helical segments flanking the putative $Ca^{2+}$ binding loop, that might contribute to the accelerated transbilayer movement of membrane phospholipids.

Example 3

Plasma Membrane Expression of Phospholipid Scramblase Regulates $Ca^{2+}$ Induced Movement of Phosphatidylserine to the Cell Surface: Alteration of Phosphatidylserine Exposure In Human Lymphoblasts Through Stable Transfection with PL Scramblase cDNA A. Summary In order to determine whether PL scramblase is responsible for the rapid movement of PS from inner-to-outer plasma membrane leaflets in other cells exposed to elevated cytosolic [$Ca^{2+}$]$_c$, we analyzed how induced movement of PS to the surface related to cellular content of PL scramblase. Exposure to $Ca^{2+}$ ionophore A23187 resulted in rapid PS exposure in those cells high in PL scramblase (K-562, HEL, 293T, and EBV-transformed lymphocytes), whereas this response was markedly attenuated in cells with low amounts of the protein (Raji, MOLT-4, HL-60). To confirm this apparent correlation between PL scramblase expression and PS egress at elevated [$Ca^{2+}$]$_c$, Raji cells were transfected with PL scramblase cDNA in pEGFP-C2, and stable transformants expressing various amounts of rGFP-PL scramblase fusion protein obtained. Clones expressing rGFP-PL scramblase showed plasma membrane-localized fluorescence and elevated PL scramblase antigen whereas clones expressing rGFP alone (transfected with pEGFP-C2 without insert) showed only cytoplasmic fluorescence and served as controls. In absence of ionophore, expression of rGFP-PL scramblase had no effect on cell viability or background PS exposure. In response to A23187, clones expressing GFP-PL scramblase exhibited markedly accelerated movement of PS to the cell surface when compared to A23187-treated clones expressing GFP with PS movement to the cell surface increasing with amount of rGFP-PL scramblase expressed. These data indicate that transfection with PL scramblase cDNA promotes [$Ca^{2+}$]$_c$-dependent movement of PS to the cell surface and suggest that this protein normally mediates redistribution of plasma membrane phospholipids in activated, injured, or apoptotic cells exposed to elevated [$Ca^{2+}$]$_c$.

B. *Materials and Methods*

Materials. All restriction enzymes were from New England BioLabs, Inc. (Beverly, Mass.). Klentaq polymerase and pEGFP-C2 vector were from CLONTECH Laboratories (Palo Alto, Calif.). Bovine coagulation factor Va (FVa), factor Xa (FXa), prothrombin and dansylarginine- N-(3-ethyl-1,5-pentanediyl)amide were from Haematologic Technologies, Inc. (Essex Junction, Vt.). Chromogenic thrombin substrate S2238 was from DiaPharma Group, Inc. (Franklin, Ohio). Human a-thrombin was a generous gift from Dr. John W. Fenton (Albany, N.Y.). OPTI-MEM and geneticin were from Life Technologies (Gaithersburg, Md.). Fetal bovine serum, RPMI 1640, Cell Dissociation Solution, Hank's Balanced Salt Solution (HBSS), Protein A Sepharose-CL4B, leupeptin, and BSA were from Sigma Chemical Co. (St. Louis, Mo.). UltraLink Iodoacetyl resin and SuperSignal ULTRA Chemiluminescence Kit were from Pierce Chemical Co. (Rockford, Ill.). All other chemicals were of reagent grade.

Cell culture: Human cancer cell lines erythroleukemic HEL, promyelocytic leukemia HL-60, chronic myelogenous leukemia K562, lymphoblastic leukemia MOLT-4, acute T-cell leukemia Jurkat, Burkitt's lymphoma Raji, and megakaryocytic DAMI were from American Type Culture Collection (Rockville, Md.) and cultured in RPMI 1640 containing 10% fetal bovine serum. EBV-transformed cell line W9 established from peripheral B-lymphocytes of a normal donor was maintained as previously described (H. Kojima, et al., 1994).

Antibodies: Anti-GFP: murine monoclonal antibody against green fluorescent protein (GFP) was from CLONTECH Laboratories. Anti-FVa: murine monoclonal antibody V237 reactive against human or bovine factor Va light chain was the generous gift of Dr. Charles T. Esmon (Oklahoma Medical Research Fndn, Oklahoma City, Okla.). Anti-PL scramblase-E306-W318: Rabbit antibody raised against the carboxyl terminal peptide sequence E306-W318 of human PL scramblase has previously been described (Q. Zhou, et al., supra, 1997). The IgG fraction was isolated on protein A-Sepharose-CL4B and the peptide-reactive antibody purified by affinity chromatography on peptide [Cys]-ESTGSQEQKSGVW (SEQ ID NO:5) coupled to UltraLink Iodoacetyl resin.

Plasmid Construction: Human PL scramblase cDNA insert was released from plasmid pMAL-C2-PL scramblase (Q. Zhou, et al., supra, 1997) by double cutting with EcoRI and SalI, respectively, and then ligated into pEGFP-C2 vector using the same restriction site. The pEGFP-C2-PL scramblase plasmid was amplified from single clones in $E.$ $coli$ strain Top 10, and the orientation and reading frame of the insert confirmed by sequencing on an ABI DNA Sequencer Model 373 Stretch (Perkin Elmer-Applied Biosystems, Foster City, Calif.) using PRISM Ready Reaction DyeDeoxy Terminator Cycle Sequencing Kit.

Transfection of Raji cells with pEGFP-PL scramblase. $1.6 \times 10^7$ Raji cells were electroporated with 160 μg plasmid DNA (pEGFP-C2-PL scramblase or pEGFP-C2) in a total volume of 0.8 ml OPTI-MEM, using Gene Pulse Electroporator (Bio-Rad Laboratories, Hercules, Calif.) set at 450 V, 500 μF. After 48 hours in culture, 1.5 mg/ml geneticin was added to the medium and continuously maintained for 4 weeks. Stable transformants exhibiting GFP fluorescence were sorted by flow cytometry (FACStar, Becton-Dickinson Immunocytometry Systems, San Jose, Calif.) using an FL1 sorting gate. The FL1-positive cells were dilutionally cloned in 96 well culture plates. pEGFP-PL scramblase transformants expressing the 62 kDa GFP-PL scramblase fusion protein were identified by Western blotting with anti-GFP and with anti-PL-306-W318 antibodies. Western blotting of pEGFP-C2 transformants (without insert) confirmed presence of 27 kDa GFP. Clones expressing various amounts of GFP-PL scramblase were each expanded for functional assay, along with comparable GFP-expressing clones serving as controls.

Fluorescence Microscopy. Cell clones transfected with pEGPF-C2-PL scramblase or pEGFP-C2 were deposited on glass microscopy slides using a Cytospin 3 (Shandon, Inc., Pittsburgh, Pa.). Phase contrast and fluorescence microscopy was performed with a ZEISS AXIOSKOP microscope (Carl Zeiss, Inc., Thornwood, N.Y.) equipped for epifluorescence, and images were recorded with a MC100 camera system. The exposure times for photography of fluorescence was 80–200 seconds under automatic control using Kodak Ektachrome 1600 film.

Western Blot Analysis. Western blotting of GFP and PL scramblase antigens was performed using $1.5 \times 10^6$ cells per lane. After washing in HBSS, supernatants were removed, and the cell pellets extracted with 2% (v/v) NP-40 in 5 mM EDTA, 50 mM benzamidine, 50 mM N-ethyl maleimide, 1 mM phenylmethylsulfonyl fluoride, 1 mM leupeptin in HBSS. After removal of insoluble material (250,000×g, 30 minutes, 4° C.), the samples were denatured at 100° C. in 10% (w/v) SDS sample buffer containing 2% β-mercaptoethanol. Following SDS-PAGE and transfer to nitrocellulose, the blocked membrane was incubated with either 10 μg/ml of rabbit anti-PL scramblase-E306–W318, or 1/10,000 dilution of mouse anti-GFP. The blots were developed with the horseradish peroxidase conjugate of either goat anti-rabbit IgG or goat anti-mouse IgG, respectively, using SuperSignal ULTRA chemiluminescence.

Measurement of cell surface PS. Calcium ionophore-induced exposure of PS on the surface of all cell lines analyzed was detected by the specific binding of coagulation factor Va (light chain) as previously described (P. J. Sims, et al., $J. \ Biol. \ Chem.$ 263:18205–18212, 1988; H. Kojima, et al., $J. \ Clin. \ Invest.$ 94:2237–2243, 1994). Briefly, cells were washed twice to remove serum proteins and suspended ($2 \times 10^6$ cells/ml) at 37° C. in RPMI 1640 supplemented with 0.1% BSA, 20 mM HEPES, and adjusted to 1.2 mM free $[Ca^{2+}]$. At time=0 A231.87 (0 or 2 μM final concentration) was added from 1 mM stock solution in DMSO, and at times indicated in figure legends, the reaction was stopped by addition of 6 mM EGTA. PS exposed on the cell surface at each time point was detected by incubating (10 minutes, room temperature) 50 μl of the cell suspension with $10^4$ g/ml FVa, followed by 10 μg/ml anti-FVa, to detect the cell-bound FVa light chain. After staining with 10 μg/ml Tri-Color conjugated goat anti-mouse IgG (CALTAG Laboratories, Burlingame, Calif.), single-cell fluorescence was quantitated by flow cytometry (FL3 channel, FACScan, Becton Dickinson Immunocytometry Systems). Use of Tri-Color conjugate to detect cell-bound FVa enabled simultaneous measurement of cell-associated GFP fluorescence in cell lines transformed with the pEGFP-C2 expression plasmid (fluorescence of GFP detected in FL1 channel). In experiments in which cell lysis was monitored by uptake of propidium iodide, cells were stained for bound FVa with FITC-conjugate of goat anti-mouse IgG (FL1 channel) substituting for Tri-Color conjugate, and propidium iodide was detected in FL3 channel. Propidium iodide (0.5 μg/ml) was added immediately before dilution for flow cytometry.

Prothrombinase Assay. Prothrombinase activity of Raji cells was determined by modification of methods previously described for platelets, using the chromogenic thrombin substrate S2238 (P. J. Sims, et al., supra, 1988). Briefly, $1 \times 10^5$ Raji cells (transfected with either pEGFP-C2 or pEGFP-C2-PL scramblase) were suspended in 200 μl HBSS containing 1% BSA in the presence of 2 nM FVa, 1.4 μM prothrombin 2.5 mM $CaCl_2$, and 4 μM dansylarginine-N-(3-ethyl-1,5-pentanediyl)amide (to inhibit feed-back activation by thrombin), and incubated at 37° C. $Ca^{2+}$-ionophore A23187 (2 $\mu$M), or DMSO (as solvent control) was added, and prothrombin conversion was initiated by addition of 2 nM Fxa. Thrombin generation was stopped after 2 minutes by dilution into 10 mM EGTA and samples were stored on ice. Aliquots were transferred to a 96-well plate, and thrombin generated was assayed in TBS containing 1% BSA in presence of 150 $\mu$M S2238 by monitoring time-dependent changes in absorbance at 405 nm using a Thermo$_{max}$ plate reader (Molecular Devices, Sunnyvale, Calif.). Thrombin activity was calculated using purified thrombin as standard.

C. Results

Figure 8A:
FIGS. 8A and 8B are Western blot analyses of PL scramblase protein (FIG. 8A) and corresponding functional assay of PL scramblase activity in various human cell lines (FIG. 8B).
Figure 8B:
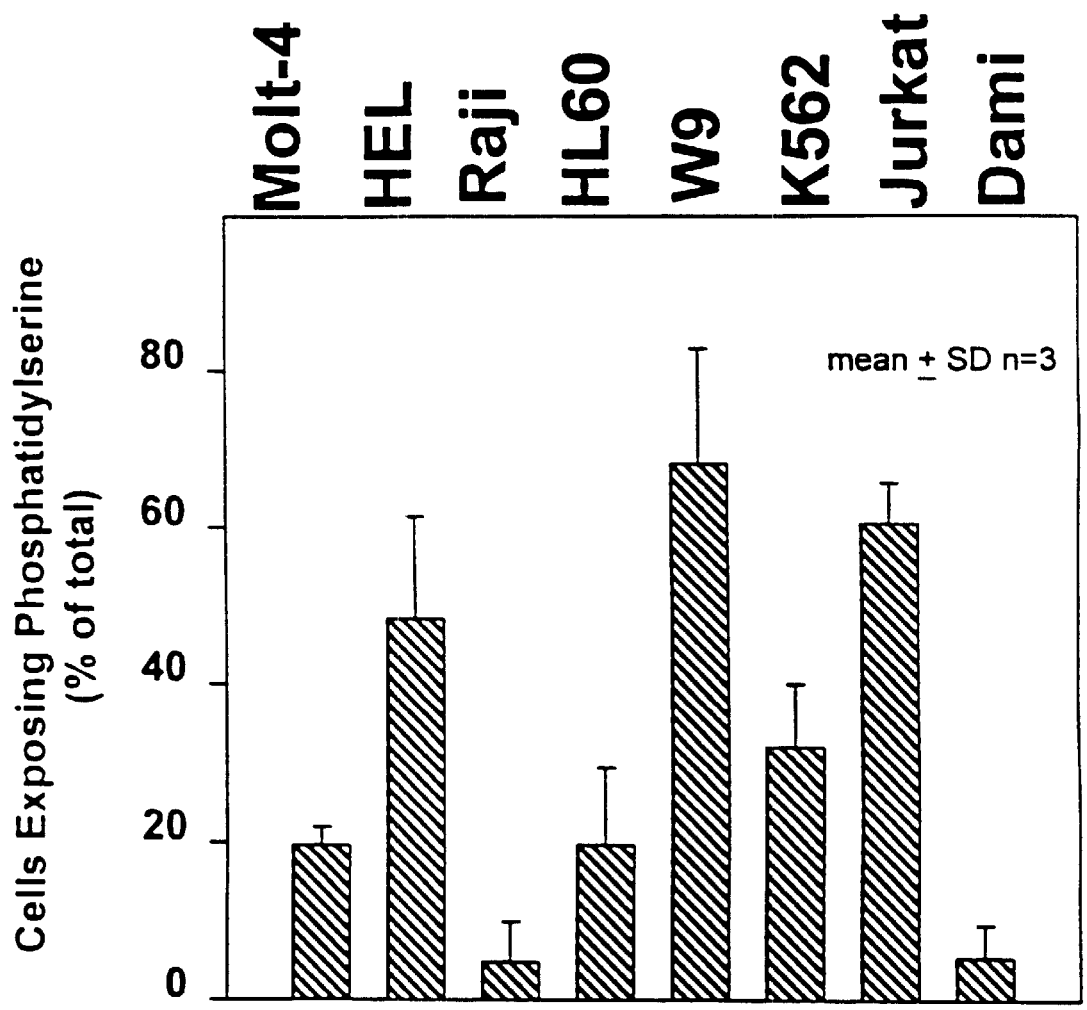

Analysis of PL scramblase in various human cell lines. Proteoliposomes reconstituted with erythrocyte PL scramblase exhibit accelerated transbilayer movement of fluorescent phospholipids in response to added $Ca^{2+}$, similar to the observed effect of calcium on the endofacial surface of the red cell membrane (Q. Zhou, et al., supra, 1997; J. G. Stout, et al., *J. Clin. Invest.* 99:2232–2238, 1997; Bassé, et al., *J. Biol. Chem.* 271:17205–17210, 1996). In order to determine whether this same protein is responsible for mediating the accelerated egress of plasma membrane PS that is observed under conditions of elevated cytosolic $[Ca^{2+}]_c$, we undertook to determine whether the level of expression of PL scramblase in various human cell lines correlated to the induced movement of PS to the surface of these cells. When challenged with a calcium ionophore, human cell lines exhibit considerable differences in the extent to which PS is mobilized to the cell surface. Among the cells tested, Raji, HL60, and Dami were notably unresponsive to A23187, whereas HEL, W9 (an EBV-transformed normal B-lymphocyte), and Jurkat showed notably robust responses. This apparent cell type-specific variability in response to induced elevation of $[Ca^{2+}]_c$ was consistently maintained through many months of passage in culture, suggesting it reflected an inherent property of each cell line. As shown in FIG. 8, we also observed considerable differences in the content of PL scramblase protein among these various cell lines, and the sensitivity of these various cell lines to induced exposure of plasma membrane PS (lower panel) generally correlated with the amount of cellular PL scramblase protein detected by Western blotting (upper panel): Those cell lines that were most responsive to induced elevation of $[Ca^{2+}]_c$ (HEL, W9, Jurkat) also expressed greatest amounts of PL scramblase antigen, whereas cell lines with attenuated response to $[Ca^{2+}]_c$ (Raji, HL60, Dami) contained relatively little of this protein. Cell lines Molt-4 and K562 showed intermediate responses to elevated $[Ca^{2+}]_c$ and expressed intermediate levels of PL scramblase antigen.

FIG. 8 depicts western blot analysis of PL scramblase in various human cell lines. Constitutive expression of PL scramblase was analyzed in the human cell lines indicated. Upper Panel: Results obtained by Western blotting with antibody specific for PL scramblase carboxyl terminal residues E306–W318 (see *Materials & Methods*). Each lane contains the total protein extract of 1.5×10⁶ cells. Lower Panel: Cumulative results of three separate experiments performed as follows: The cells indicated were washed and suspended at 37° C. in the presence of 1.2 mM free $Ca^{2+}$ and 2 $\mu$M A23187 was added. At times shown (abscissa), EGTA was added and cells analyzed for surface exposed PS as detected by cell-bound FVa light chain (see *Materials and Methods*). Data plotted represent the mean increase (±SD) in number of cells that stained positive for surface PS after 5 minutes incubation with ionophore, after correction for initial background of PS-positive cells before addition of ionophore (time=0). Background number of cells that exposed PS in absence of ionophore was always <15% except in case of HEL, where this background ranged between 15–30%.

These relatively large differences in cell line-specific expression of this protein was also consistently observed despite repeated passage in culture, and was found to correspond to marked differences in level of specific mRNA as detected by Northern blotting with PL scramblase cDNA (Q. Zhou, et al., supra, 1997), and data not shown). We also noted that those cell lines with the highest content of PL scramblase generally exhibited a higher background of PS exposed on the surface in absence of added ionophore. This was most notable for HEL for which approximately 15–30% of the cells were consistently found to expose PS prior to addition of A23187 ( see Discussion).

Membrane chances underlying ionophore response. In order to determine whether the increase in PS exposure in ionophore-treated cells reflected facilitated movement of PS from inner to outer leaflets of the plasma membrane, or, greater sensitivity of the plasma membrane to lytic disruption, FVa binding to the cell surface was monitored simultaneously with uptake of propidium iodide, as a measure of cell lysis. As illustrated for the human B-lymphocyte lines W9 (high content of PL scramblase) and Raji (low content of PL scramblase), the induced movement of PS to the cell surface was found to precede uptake of propidium iodide, suggesting that the elevation of $[Ca^{2+}]_c$ induces a collapse of transmembrane PL asymmetry before onset of lysis. In the case of Raji cells which are virtually devoid of PL scramblase (see FIG. 8), a general insensitivity of the plasma membrane to either ionophore-induced PS exposure or to lysis was also apparent.

Figure 9:
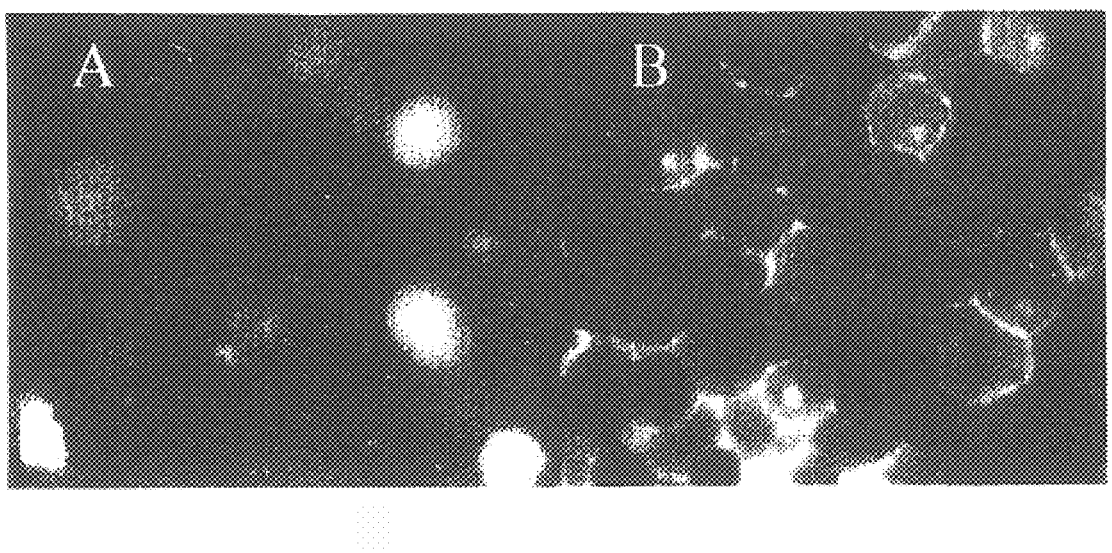
FIGS. 9A and B are fluorescence micrographs of GFP-PL scramblase in transformed Raji cells.
FIG. 9B depicts cells transfected with pEGFP-C2-PL scramblase plasmid and expressing GFP-PL scramblase fusion protein.

Transfection of the Raji cell line with pEGFP-C2-PL scramblase. In order to confirm that the extent to which PS moves to the cell surface with elevation of $[Ca^{2+}]_c$ actually depends upon the plasma membrane content of PL scramblase, we stably transformed Raji, a cell line exhibiting low endogenous PL scramblase expression by transfection with plasmid pEGFP-C2-PL scramblase. This plasmid expresses PL scramblase as a fusion protein with green fluorescent protein (GFP), facilitating flow cytometric sorting of transformants for subsequent cloning and detection of the expressed recombinant protein in selected clones. The decision to attach GFP to the amino terminus of PL scramblase was based on prior evidence that the carboxyl terminus of the protein is membrane inserted and essential for function, and the observation that other amino terminal fusion constructs of PL scramblase expressed in *E. coli* retained the same activity of the unmodified PL scramblase polypeptide when reconstituted in proteoliposomes (Q. Zhou, et al., supra, 1997), and unpublished data). The expression of the full-length GFP-PL scramblase fusion protein in selected transformed clones was confirmed by Western blotting with antibody specific for GFP, and with antibody raised against peptide sequence of the carboxyl terminus of human PL scramblase. As illustrated by fluorescence micrographs shown in FIG. 9, clones that expressed the GFP-PL sctamblase fusion protein showed a distinct rim appearing pattern of fluorescence, consistent with trafficking of GFP-PL scramblase to the plasma membrane. FIG. 9 illustrates fluorescence micrographs of GFP-PL scramblase transformed Raji cells. Fluorescence photomicrography of GFP fluorescence expressed in the transformed Raji clones was performed as described in *Materials and Methods*. FIG. 9A shows fluorescence of cells expressing GFP; FIG. 9B shows cells transfected with pEGFP-C2-PL scramblase plasmid and expressing GFP-PL scramblase fusion protein. Data of single experiment, representative of results obtained for all clones transfected with either pEGFP-C2 or pEGFP-C2-PL scramblase. By contrast, clones that expressed GFP alone exhibited diffuse fluorescence throughout the cytoplasm, with no obvious staining of the plasma membrane. These data provide the first direct evidence that PL scramblase CDNA encodes a protein that predominantly traffics to the plasma membrane under normal conditions of cell growth.

Analysis of PS mobilizing function in GFP-PL scramblase transformants. After geneticin selection, clonal populations of transformed Raji cells expressing comparable levels of either GFP-PL scramblase or GFP (transformed with pEGFP-C2 lacking insert) were analyzed for their capacity to mobilize PS to the cell surface. In response to an A23187-induced elevation of $[Ca^{2+}]_c$, transformants expressing the GFP-PL scramblase fusion construct showed a marked increase in both the rate and extent that PS became exposed on the cell surface, when compared to either the identically-treated parental Raji cell line or to GFP-expressing clones transformed with pEGFP-C2 vector alone. As was also evident from these data, in the absence of ionophore, we consistently noted a small but reproducible increase in the background level of PS exposure in transformants expressing GFP-PL scramblase protein, when compared to either the parental Raji cell lines or to GFP-expressing clones transformed with vector alone.

Induction of membrane procoagulant function through expression of PL scramblase. In order to confirm that the increased expression of FVa binding sites detected upon activation of GFP-PL scramblase transformed clones reflected an increase in the procoagulant (clot-promoting) properties of the plasma membrane of these cells, the capacity of GFP-PL scramblase transformed cells to provide catalytic membrane surface for the prothrombinase (FVaXa) enzyme complex was compared to clones expressing GFP alone. These data confirmed that expression of recombinant PL scramblase in the Raji cell line was also accompanied by an increase in cell capacity to catalyze the prothrombinase reaction upon entry of calcium into the cytosol.

Figure 10:
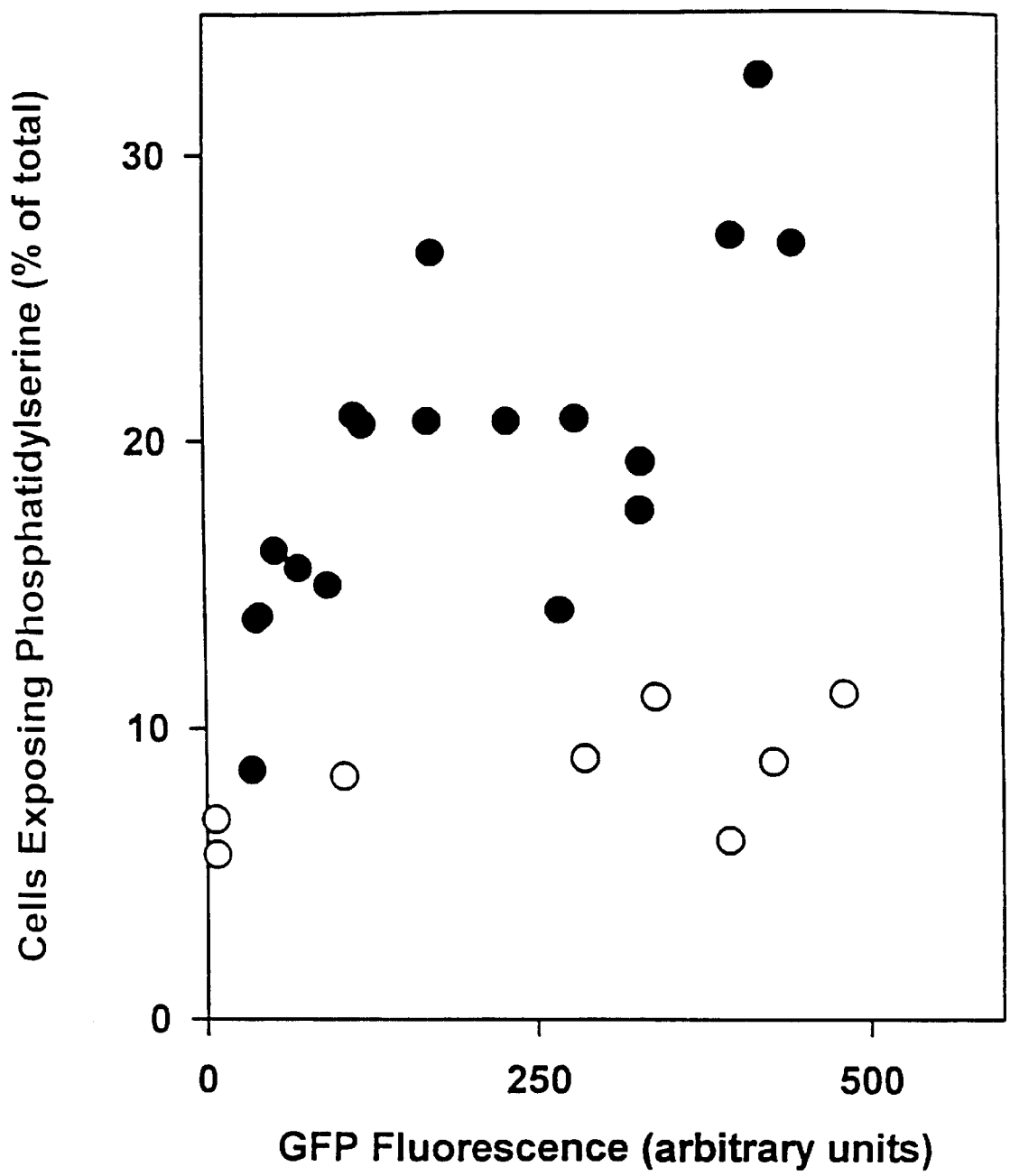
FIG. 10 is a graph showing that the level of expression of PL scramblase determines plasma membrane sensitivity to intracellular calcium.

Level of expression of PL scramblase regulates capacity of to mobilize PS to-the cell surface. In order to confirm the apparent correlation between endogenous cell content of PL scramblase and plasma membrane sensitivity to elevated $[Ca^{2+}]_c$ that is evident when different human cell lines are compared (see FIG. 8), we analyzed multiple Raji clones that were stably transfected with either GFP-PL scramblase or with GFP vector alone (FIG. 10). FIG. 10 illustrates that the level of expression of PL scramblase determines plasma membrane sensitivity to intracellular $Ca^{2+}$. The relationship between level of recombinant protein expressed (GFP fluorescence detected in FL1 channel; abscissa) and numbers of cells that expose PS after 2 minutes incubation with A23187 (ordinate) is plotted for multiple transformed Raji clones. Analysis was gated to include only those cells distinctly positive for GFP fluorescence (FL1 channel), and cell-bound FVa was stained with Tri-color conjugate and detected in FL3 channel (see *Materials and Methods*). Analysis was performed on all cells positive for GFP fluorescence.

Open symbols indicate individual clones stably transformed by transfection with pEGFP-C2; closed symbols indicate individual clones stably transformed with pEGFP-PL scramblase. Data of single experiment, representative of three so performed. These experiments confirm that the capacity of GFP-PL scramblase transformants to mobilize PS to the cell surface generally correlates with the amount of the expressed GFP-PL scramblase fusion protein, whereas this cell response to increased $[Ca^{2+}]_c$ is unaffected by cell content of GFP. In addition to confirming the role of PL scramblase in the plasma membrane response to $[Ca^{2+}]_c$, these data suggest that the capacity to mobilize PS to the cell surface and thereby support plasma clotting in activated, injured or apoptotic cells exposed to elevated $[Ca^{2+}]_c$ can be altered by changing the level of expression of PL scramblase expressed in the plasma membrane.

Discussion

These results provide the first evidence that the PL scramblase protein identified in the erythrocyte membrane and implicated in $[Ca^{2+}]$-induced remodeling of membrane phospholipids actually functions to induce accelerated transbilayer movement of plasma membrane phospholipid in human cells that express this protein. Our results also confirm that the level of expression of plasma membrane PL scramblase can determine the extent to which PS is mobilized to the cell surface upon elevation of $[Ca^{2+}]_c$, and suggest that this protein normally functions to mediate the redistribution of plasma membrane phospholipids in response to the entry of calcium into the cytosol. Furthermore, these data provide the first indication that the movement of PS and other procoagulant aminophospolipids from plasma membrane inner leaflet to the cell surface can be manipulated by selectively altering the level of expression of a particular cellular protein, either through direct transfection with the PL scramblase cDNA, or potentially, by another intervention affecting cellular expression of functional PL scramblase protein.

Whereas these experiments suggest that direct activation of plasma membrane PL scramblase is responsible for the increased cell surface exposure of PS that is observed in various activated, injured or apoptotic cells exposed to elevated $[Ca^{2+}]_c$, we cannot exclude the possibility that there are other cellular components that contribute to the accelerated movement of PS from inner to outer plasma membrane leaflet under these conditions. In particular, whereas PL scramblase has been shown to mediate the bidirectional movement of PS and other phospholipids between membrane leaflets, it has been suggested that there is also a PS-selective pathway in the platelet plasma membrane, designated "PS floppase", which mediates vectorial movement of PS from inner to outer plasma membrane leaflet (P. Gaffet, et al., *Biochemistry* 34:6762–6769. 1995). Experimental evidence for the existence of this vectorial and headgroup-selective PS floppase pathway in platelet or other cell membranes remains controversial (R. F. A. Zwaal, et al., supra, 1997; P. Williamson, et al., *Biochemistry* 31:6355–6360, 1995; C. -P. Chang, et al., *J. Biol. Chem.* 268:7171–7178, 1993), and awaits identity of a $[Ca^{2+}]_c$-activated and PS-selective transporter that is distinct from the plasma membrane PL scramblase found in platelets and erythrocytes, a protein that does not exhibit apparent selectivity for the PS headgroup (J. G. Stout, et al., supra, 1997; P. Comfurius, et al., *Biochemistry* 35,7631–7634, 1996; F. Bassé, et al., supra, 1996).

In addition to conferring increased sensitivity of the plasma membrane to ionophore-induced elevation of $[Ca^{2+}]_c$, we generally observed a higher background of PS exposure (in absence of ionophore) in those transfected cell clones expressing large amounts of the GFP-PL scramblase fusion protein. This elevated background PS exposure was also observed in the case of untreated HEL, the cell line containing the highest endogenous content of PL scramblase. Although we suspect that this increased background reflects the enhanced sensitivity of the plasma membrane of these cells to any adventitial elevation of $[Ca^{2+}]_c$ during cell processing for assay, we cannot exclude the possibility that these cells are also inherently more fragile due to the large amounts of PL scramblase that is inserted into the plasma membrane.

While the movement of plasma membrane PS to the cell surface at elevated $[Ca^{2+}]_c$ can be demonstrated in a variety of cells and tissues (R. F. A. Zwaal, et al., supra, 1997; P. Devaux, supra, 1991), we detect marked differences in the levels of PL scramblase mRNA and protein among different human cell types, which is generally reflected by corresponding differences in sensitivity to this $[Ca^{2+}]$-induced collapse of plasma membrane PL asymmetry (see FIG. 8, and Q. Zhou, et al., supra, 1997). Although the transcriptional regulation of the PL scramblase gene remains to be determined, it is of interest to note that such cell or tissue-specific differences in PL scramblase expression has the potential to significantly affect the biological properties of the cell. In particular, we note that the content of PL scramblase in human platelet is approximately 10-fold greater than that of the erythrocyte, which is consistent with the respective PS-mobilizing potential and different roles of these two cells in contributing procoagulant membrane surface for thrombin generation during blood clotting (Q. Zhou, et al., supra, 1997). In addition to the relatively high levels of PL scramblase identified in circulating human platelets, this protein was also most abundant in the cell line HEL, whereas only small amounts of this protein (and low PL scramblase activity) was detected for Dami (FIGS. 8), two human cancer cell lines exhibiting partial megakaryocytic-like properties. It is also noteworthy that several of the lymphoma-derived cell lines (e.g., Raji, MOLT-4) express considerably reduced levels of PL scramblase, and also show distinctly attenuated PS exposure in response to elevated $[Ca^{2+}]_c$, when compared to either peripheral blood leukocytes or to EBV-transforms of normal lymphocytes (FIG. 8). The collapse of plasma membrane phospholipid asymmetry is a relatively early event in apoptosis of lymphocytes and other cells, and the consequent exposure of PS on the cell surface is thought to contribute to phagocytic removal of such cells by scavenger macrophages (V. A. Fadok, et al., J. Immunol. 148:2207–2216, 1992; B. Verhoven, et al., J. Exp. Med. 182:1597–1601, 1995). It is therefore of interest to consider whether the apparent resistance of certain lymphoma-derived cell lines to such $[Ca^{2+}]$-induced remodeling of plasma membrane phospholipids might contribute to the proliferative potential and in vivo survival of these or other transformed cells.

Example 4

Inactivation of Human PL Scramblase by Treatment With the Thiolester Cleaving Reagent, Hydroxylamine A. Summary Incubation of human erythrocyte PL scramblase with hydroxylamine under conditions known to favor hydrolysis of protein cysteinyl-fatty acyl bonds was found to cause near complete loss of PL scramblase's function in promoting movement of PL between membrane leaflets. These data suggest that for normal activity, the PL scramblase polypeptide requires post translational modification through addition of a thiolester-linked fatty acid. Furthermore, these data imply that methods that either prevent cellular acylation of the polypeptide, or that cleave cysteinyl thiolester linkages, will effectively inhibit endogenous PL scramblase activity.

B. Methods

Protein purification. PL scramblase was purified from human erythrocyte ghost membranes as previously described (F. Bassé, et al.,supra, 1996; J. G. Stout, et al., supra, 1997).

Treatment with Hydroxylamine. PL scramblase was incubated 1 hour room temperature in 1 M hydroxylamine, 25 mM octylglucoside, 1 M Tris-HCl at pH 7.4. Match control samples of the protein were identically incubated under these conditions, omitting hydroxylamine. After incubation, samples were dialyzed and reconstituted into PL proteoliposomes for assay of PL scramblase activity.

Membrane reconstitution and assay. PL scramblase was reconstituted into proteliposomes and activity determined as previously described(F. Bassé, et al., supra, 1996; J. G. Stout, et al, supra, 1997).

C. Results and Discussion

Figure 11:
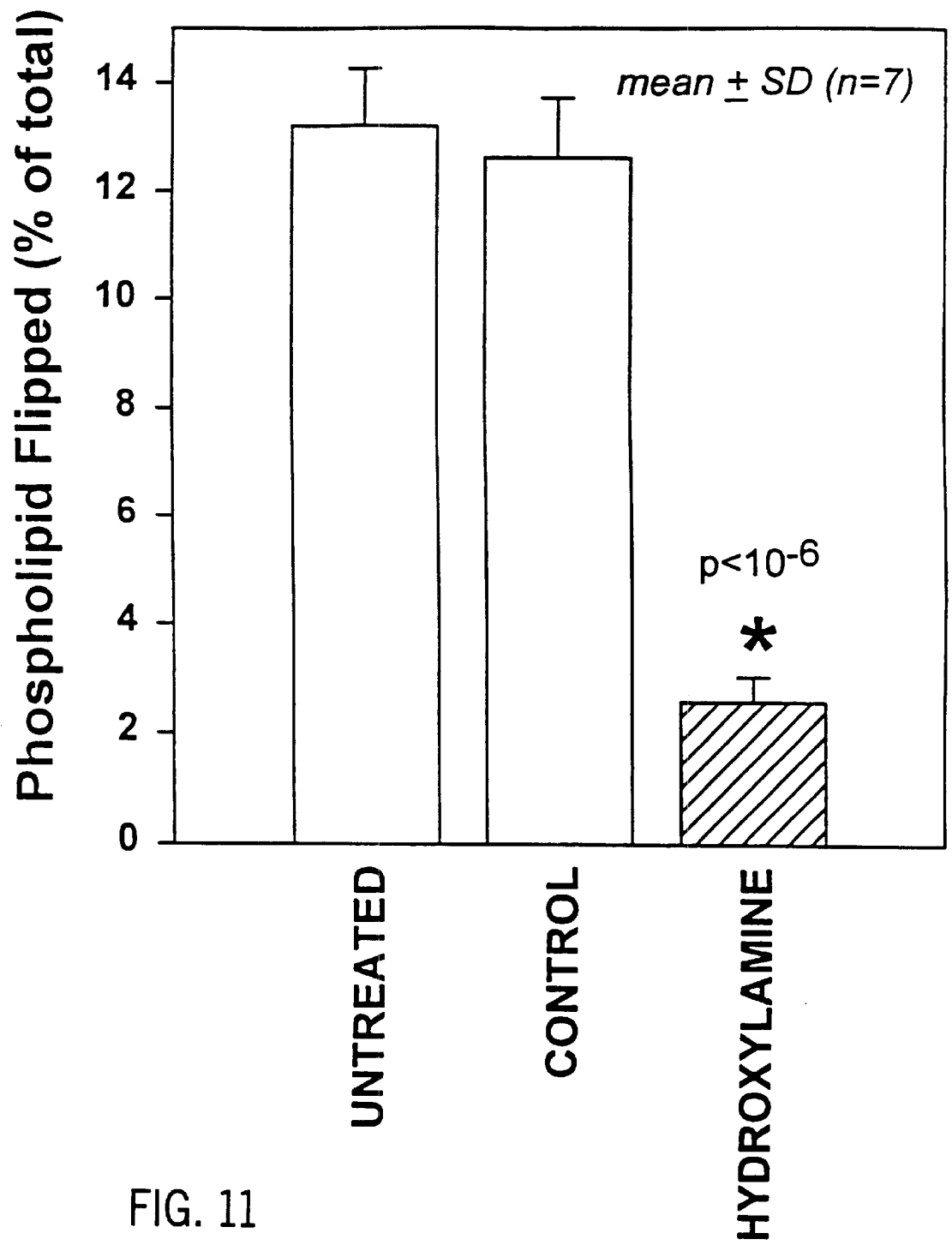
FIG. 11 is a bar graph illustrating inactivation of PL scramblase by hydroxylamine.

As shown in FIG. 11, incubation with hydroxylamine resulted in nearly complete inactivation of PL scramblase. FIG. 11 illustrates inactivation of PL scramblase by hydroxylamine. Purified human erythrocyte PL scramblase was incubated 1 hour, room temperature, in the presence of 50 mM octylglucoside, 1M TrisHCl, and either 0 (control) or 1M (hydroxylamine) hydroxylamine at pH 7.2. Untreated refers to sample maintained in low ionic strength sample buffer at 4° C. . Each sample was then dialyzed and reconstituted into proteoliposomes for assay of PL scramblase activity using NBD-PC as detailed in Bassé, et al., supra, 1996 with modifications of Stout, et al., supra, 1997. Ordinate indicates percent of total NBD-PC flipped during 3 hours. Incubation was in 2 mM $Ca^{2+}$, with correction for background measured in 0.1 mM EGTA. The error bars denote mean±SD, n=7. Combined data of three independent experiments performed on different days.

Because the conditions of incubation (neutral pH) were chosen to favor specific cleavage of cysteinyl thioester bonds without disulfide bond reduction, these results imply an essential thioester linkage within the protein. In a membrane-associated protein with cytoplasmic Cys residues, such as found in erythrocyte PL scramblase, this thiolester bond is normally provided by palmitic acid in ester linkage to one or more cysteinyl thiols.(H. Schroeder, et al., J. Cell Biol. 134:647–660, 1996; M. Stauffenbiel, J. Biol. Chem. 263:13615–13622, 1988; C. A. Wilcox, et al., Biochemistry 26:1029–1036, 1987). Whereas the possibility of disulfide reduction by hydroxylamine cannot be excluded, it is important to note that (1) virtually all cysteine residues in PL scramblase are normally exposed to cytoplasmic reducing agents such as glutathione, and disulfide bonds formation is therefore not anticipated and (2) The absence of any functionally-important disulfide bonds in PL scramblase can be assumed based on the retention of normal PL scramblase activity when the protein was incubated in various reducing agents, including dithiothreitol (F.

Bassé, et al., supra, 1996; J. G. Stout et al., supra, 1997). Thus these data suggest that PL scramblase polypeptide requires post-translational modification through addition of a thiolester-linked fatty acid for its normal function in the plasma membrane. Furthermore, these data imply that reagents that either prevent cellular acylation of the polypeptide, or, reagents that cleave cysteinyl thiolester linkages, will effectively inhibit endogenous PL scramblase activity.

We claim:

1. A recombinant DNA sequence encoding human or murine PL scramblase wherein the sequence has been modified to prevent post-translational phosphorylation or palmitoylation modification in the encoded PL scramblase wherein the sequence comprises a mutation with a substitution of residue Thr161 of SEQ ID NO:2; Thr159 of SEQ ID NO:4 or the equivalent residue in the conserved region of another PL scramblase.

2. A recombinant DNA sequence encoding human or murine PL scramblase wherein the sequence has been modified to prevent post-translational phosphorylation or palmitoylation modification in the encoded PL scramblase wherein the sequence comprises at least one substitution within residues Asp273–Asp284 of SEQ ID NO:2; Asp271–Asp282 of SEQ ID NO:4 or the equivalent residue in the conserved region of another PL scramblase.

* * * * *

UNITED STATES PATENT AND TRADEMARK OFFICE
CERTIFICATE OF CORRECTION

PATENT NO.   : 6,534,640 B1
DATED        : March 18, 2003
INVENTOR(S)  : Therese Wiedmer et al.

It is certified that error appears in the above-identified patent and that said Letters Patent is hereby corrected as shown below:

Column 1,
Line 35, "])" should read -- ]c) --.

Column 3,
Line 8, "conserved 25 in" should read -- conserved in --.

Column 7,
Line 47, "is o longer" should read -- is no longer --.

Column 10,
Line 11, "These.data" should read -- These data --.
Line 15, "blocking-access" should read -- blocking access --.

Column 11,
Lines 4 and 7, "32p" should read -- 32P --.

Column 13,
Line 13, "CDNA" should read -- cDNA --.

Column 14,
Line 32, "primerss 5'" should read -- primers 5' --.

Column 15,
Lines 29 and 30, "spectrof lurimeter" should read -- spectroflurimeter --.
Line 34, "Was" should read -- was --.

Column 16,
Line 32, "CDNA" should read -- cDNA --.
Line 62, "PL S scramblase" should read -- PL scramblase --.

Column 19,
Line 44, "Sscramblase" should read -- Scramblase --.

Column 20,
Line 51, "CDNA" should read -- cDNA --.

UNITED STATES PATENT AND TRADEMARK OFFICE
CERTIFICATE OF CORRECTION

PATENT NO.     : 6,534,640 B1
DATED          : March 18, 2003
INVENTOR(S)    : Therese Wiedmer et al.

It is certified that error appears in the above-identified patent and that said Letters Patent is hereby corrected as shown below:

Column 21,
Line 19, "CDNA'" should read -- cDNA --.

Column 25,
Line 4, "Human a" should read -- Human alpha --.

Column 26,
Line 37, "time=0," should read -- time=0 --.
Line 42, "10(4) g/ml" should read -- 10(4) microg/ml --.

Column 28,
Line 17, "chances" should read -- changes --.
Line 59, "sctamblase" should read -- scramblase --.

Column 29,
Line 8, "CDNA" should read -- cDNA --.
Line 43, "to-the'" should read -- to the --.

Column 30,
Line 14, "]-induced" should read -- ]c-induced- --.

Column 31,
Line 13, "]-induced" should read -- ]c-induced --.
Line 46, "]-induced" should read -- ]c-induced --.

Signed and Sealed this

Seventh Day of October, 2003

JAMES E. ROGAN
*Director of the United States Patent and Trademark Office*